(12) United States Patent
Taniguchi et al.

(10) Patent No.: US 8,980,953 B2
(45) Date of Patent: Mar. 17, 2015

(54) ALKALINE DECOMPOSITION PRODUCT OF HOP EXTRACT AND USE THEREOF

(75) Inventors: Yoshimasa Taniguchi, Yokohama (JP); Fumitoshi Manabe, Yokohama (JP); Yumie Kobayashi, Nishinomiya (JP); Mikio Katayama, Yokohama (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 68 days.

(21) Appl. No.: 13/377,392

(22) PCT Filed: Jun. 11, 2010

(86) PCT No.: PCT/JP2010/059970
§ 371 (c)(1),
(2), (4) Date: Feb. 17, 2012

(87) PCT Pub. No.: WO2010/143719
PCT Pub. Date: Dec. 16, 2010

(65) Prior Publication Data
US 2012/0270950 A1    Oct. 25, 2012

(30) Foreign Application Priority Data

Jun. 12, 2009  (JP) ................................ 2009-141316

(51) Int. Cl.
| | |
|---|---|
| A61K 31/122 | (2006.01) |
| C12C 3/00 | (2006.01) |
| A23L 1/221 | (2006.01) |
| C07C 49/573 | (2006.01) |
| C07C 45/78 | (2006.01) |
| A61K 36/185 | (2006.01) |
| A23L 1/30 | (2006.01) |
| C12C 3/12 | (2006.01) |

(52) U.S. Cl.
CPC .............. *A61K 36/185* (2013.01); *A23L 1/221* (2013.01); *A23L 1/3002* (2013.01); *A61K 31/122* (2013.01); *C12C 3/12* (2013.01); *A23V 2002/00* (2013.01)

USPC .......... 514/690; 428/600; 428/655; 568/379; 568/341

(58) Field of Classification Search
None
See application file for complete search history.

(56) References Cited

U.S. PATENT DOCUMENTS 3,839,588 A  * 10/1974  Sweett et al.
3,956,513 A     5/1976  Clarke et al.
(Continued)

FOREIGN PATENT DOCUMENTS

EP    1481671 A1    12/2004
GB    1171341       11/1969
(Continued)

OTHER PUBLICATIONS

Hiroaki Yajima et al., "Beer Nigami Seibun no Shibo Chikuseki Yokusei Sayo (Fat Accumulation Inhibitory Effect of Beer Bittering Component)", The Japanese Society of Nutrition and Food Science Sokai Koen Yoshishu, 2003, p. 242, 3D-07p, vol. 57.
(Continued)

*Primary Examiner* — Brian-Yong Kwon
*Assistant Examiner* — Kyung Sook Chang
(74) *Attorney, Agent, or Firm* — Sughrue Mion, PLLC

(57) ABSTRACT

According to the present invention, there are provided a food and a food additive obtained using an alkaline decomposition product of a hop extract, and an agent for suppressing fat accumulation or for suppressing weight gain comprising the same as an active ingredient.

13 Claims, 14 Drawing Sheets

(56) References Cited

U.S. PATENT DOCUMENTS

| | | | |
|---|---|---|---|
| 4,758,445 | A | 7/1988 | Klüsters |
| 4,844,912 | A | 7/1989 | Haas et al. |
| 4,844,939 | A | 7/1989 | Todd, Jr. |
| PP12,404 | P2 * | 2/2002 | Zimmermann |
| 2003/0185934 | A1 * | 10/2003 | Ting et al. .................. 426/16 |
| 2006/0233902 | A1 * | 10/2006 | Yajima et al. ............... 424/778 |
| 2007/0254086 | A1 | 11/2007 | Faltermeier et al. |

FOREIGN PATENT DOCUMENTS

| | | |
|---|---|---|
| JP | 50-123854 A | 9/1975 |
| JP | 61-238754 A | 10/1986 |
| JP | 63-196260 A | 8/1988 |
| JP | 06-98738 A | 4/1994 |
| JP | 2007-289185 A | 11/2007 |
| WO | 2009023710 A2 | 2/2009 |

OTHER PUBLICATIONS

English translation of International Preliminary Report on Patentability for PCT/JP2010/059970 dated Jan. 26, 2012.

Extended Search Report issued in corresponding European Patent Application 10786250.0 on Jan. 28, 2013.

Harvey T. Chan et al., "Development of Off-Odors and Off-Flavors in Papaya Puree", J. Agr. Food Chem., 1973, 21(4): 566-570.

Database WPI, Week 199419, Thomson Scientific, London, GB, AN 1994-155902, (XP002689048), retrieved from C:\EPOPROGS\SEA\. \.. \.. \epodata\sea\eplogf\internal.log on Jan. 22, 2013.

Database WPI, AN 2001-642013, (XP002392536), "Lipase inhibitor for preventing obesity and for use in health food, feed and cosmetics, comprises crude drug or its extract such as guava leaf, hop, *Apocynum venetum* leaf, *Gymnema* leaf and/or *Gardenia fructus*", Derwent, Aug. 21, 2001, Abstract.

Database WPI, Week 200322, Thomson Scientific, London, GB, AN 2003-224029, (XP002689526), "Preparation of rice bran oil containing (gamma)-orizanol for use in cosmetics, by extracting crude oil from rice bran and purifying by degumming-, wax removing- and deoxidation-process", retrieved from C:\EPOPROGS\SEA\. \.. \.. \epodata\sea\eplogf/internal.log on Jan. 22, 2013.

Database WPI, Week 200703, Thomson Scientific, London, GB, AN 2007-021109, (XP002689091), retrieved from C:\EPOPROGS\SEA\. \.. \.. \epodata\sea\eplogf\internal.log on Jan. 22, 2013.

W. Hartmeier et al., "Removal of unwanted fatty acids from plant oils by native and immobilized lipases", Med. Fac. Landbouww. Univ. Gent., 1995, 60(4a): 1843, Abstract.

Silvester, D. J., "Simultaneous Determination of a, β and Iso-a Acids in Hops and Hop Products", The Journal of the Institute of Brewing, Sep.-Oct. 1984, pp. 319-322, vol. 90, No. 5.

Yajima, Hiroaki, et al., "Beer Nigami Seibun no Shibo Chikuseki Yokusei Sayo", The Japanese Society of Nutrition and Food Science Sokai Koen Yoshishu, 2003, p. 242, 3D-07p, vol. 57.

Office Action issued in counterpart Japanese Patent Application No. 2011-518589, dated Feb. 12, 2014.

Verzele et al., "Preparative Liquid Chromatography of Hop and Beer Bitter Acids", Journal of Chromatography, 1989, 484:361-368.

Communication from the Japanese Patent Office, dated Nov. 21, 2014, issued in counterpart Japanese Application No. 2011-518589.

Simpson et al., "Factors Affecting Antibacterial Activity of Hop Compounds and their Derivatives", Journal of Applied Bacteriology, vol. 72, No. 4, 1992, pp. 327-334.

Drewett et al., "Humulinic Acid in Isomerized Hop Extracts", Journal of the Institute of Brewing, vol. 76, No. 1, 1970, Abstract.

Hashimoto, H., "The Bitter Substances of Hops and Beer. V. A New Crystalline Bitter Substance of Beer in Fraction C", Hakko Kogaku Zasshi, vol. 39, 1961, Abstract.

* cited by examiner

ALKALINE DECOMPOSITION PRODUCT OF HOP EXTRACT AND USE THEREOF

TECHNICAL FIELD

The present invention relates to an alkaline decomposition product of a hop extract and use thereof. Specifically, the present invention relates to a food and a food additive obtained using the alkaline decomposition product of the hop extract as well as an agent for suppressing fat accumulation and an agent for suppressing weight gain which comprise the same as an active ingredient.

BACKGROUND ART

Many health conscious foods and drinks have been developed in recent years and have also been commercially available. For obtaining real products that produce an actual feeling of health functions, an amount exceeding an effective amount is required to be added, as a matter of course. So-called functional components, which impart useful effects to human bodies, are often accompanied with bitterness, as has been said that "bitters do good to the stomach" since long ago. These functional components, when contained in effective amounts or more in foods and drinks, reduce palatability and reduce the appeal of the products.

Hops, which are the origin of a bitter component in beer, have also been used as a folk medicine since long ago and are known to have various health functions such as sedative effect and stomachic effect. An extract obtained from this hop, when contained in the predetermined amount or more in foods and drinks, causes peculiar strong bitterness and might impair palatability.

Many attempts have been reported for removing or reducing such bitterness. Examples of substances used as bitterness reducing materials include phosphatidic acid (trade name "BENECOAT BMI", Kao Corp.) and L-ornithine (Food Science Journal, No. 317, p. 54, 2004). However, their effects are not always strong when used alone. Particularly, it has been difficult to reduce the bitterness of the hop extract. Moreover, in a masking technique using a sweetener such as sucralose or thaumatin as an additive (Japanese Patent Laid-Open Publication No. 2008-99682), bitterness is masked to some degree by sweetness. However, its use is limited due to the strong sweetness.

For pharmaceutical products, usually, sugar coating is mainly performed for tablets. In addition, a film coating technique, microencapsulation, or the like is used. However, it has been difficult to completely mask bitterness. Furthermore, these techniques cannot be used for liquid preparations, like drinks. Thus, the reduction of bitterness is still a significant challenge to the field of foods and drinks or pharmaceutical products.

LITERATURE LIST

Patent Literature

Patent Literature 1: Japanese Patent Laid-Open Publication No. 2008-99682
Patent Literature 2: WO2003/068205

Non Patent Literature

Non Patent Literature 1: Food Science Journal, No. 317, p. 54, 2004

SUMMARY OF THE INVENTION

Technical Problem to be solved

It has previously been reported that hop extract-derived isohumulone has PPAR agonistic effect and has a lipid metabolism improving function via this agonistic effect (WO2003/068205). However, isohumulone has strong bitterness. Thus, the reduction of its bitterness has been a challenge to the application of isohumulone to foods and drinks or pharmaceutical products.

Solution to Problem

The present inventors have found that a decomposition product obtained by subjecting an hop extract to an alkaline decomposition treatment has fat accumulation suppression effect and weight gain suppression effect though it has a drastically reduced isohumulone content, and the decomposition product has drastically reduced bitterness. The present invention is based on these findings.

Specifically, according to the present invention, there are provided a food additive comprising an alkaline decomposition product of a hop extract (hereinafter, also simply referred to as a "food additive according to the present invention"), and a food obtainable by adding the alkaline decomposition product of the hop extract (hereinafter, also simply referred to as a "food according to the present invention").

According to the present invention, there is also provided an agent for suppressing fat accumulation or for suppressing weight gain comprising the alkaline decomposition product of the hop extract as an active ingredient (hereinafter, also simply referred to as a "suppression agent according to the present invention").

According to the present invention, there are further provided a method of producing the alkaline decomposition product of the hop extract added to the food according to the present invention and a method of producing the suppression agent according to the present invention, which comprise subjecting an hop extract to an alkaline treatment and subsequently removing a fatty acid formed by the treatment.

According to the present invention, there are further provided a method of suppressing fat accumulation and a method of suppressing weight gain, which comprises administering the alkaline decomposition product of the hop extract to a mammal including a human.

According to the present invention, there is provided use of the alkaline decomposition product of the hop extract for production of an agent for suppressing fat accumulation or for suppressing weight gain.

The alkaline decomposition product of the hop extract has fat accumulation suppression effect and/or weight gain suppression effect and is also free from strong bitterness as produced by an isomerized hop extract. Thus, the food according to the present invention and the suppression agent according to the present invention are advantageous in that they can be ingested directly without taking the means of masking bitterness, while physiological activities such as fat accumulation suppression and weight gain suppression can be expected.

DETAILED DESCRIPTION OF THE INVENTION

Alkaline Decomposition Product

Figure 1:
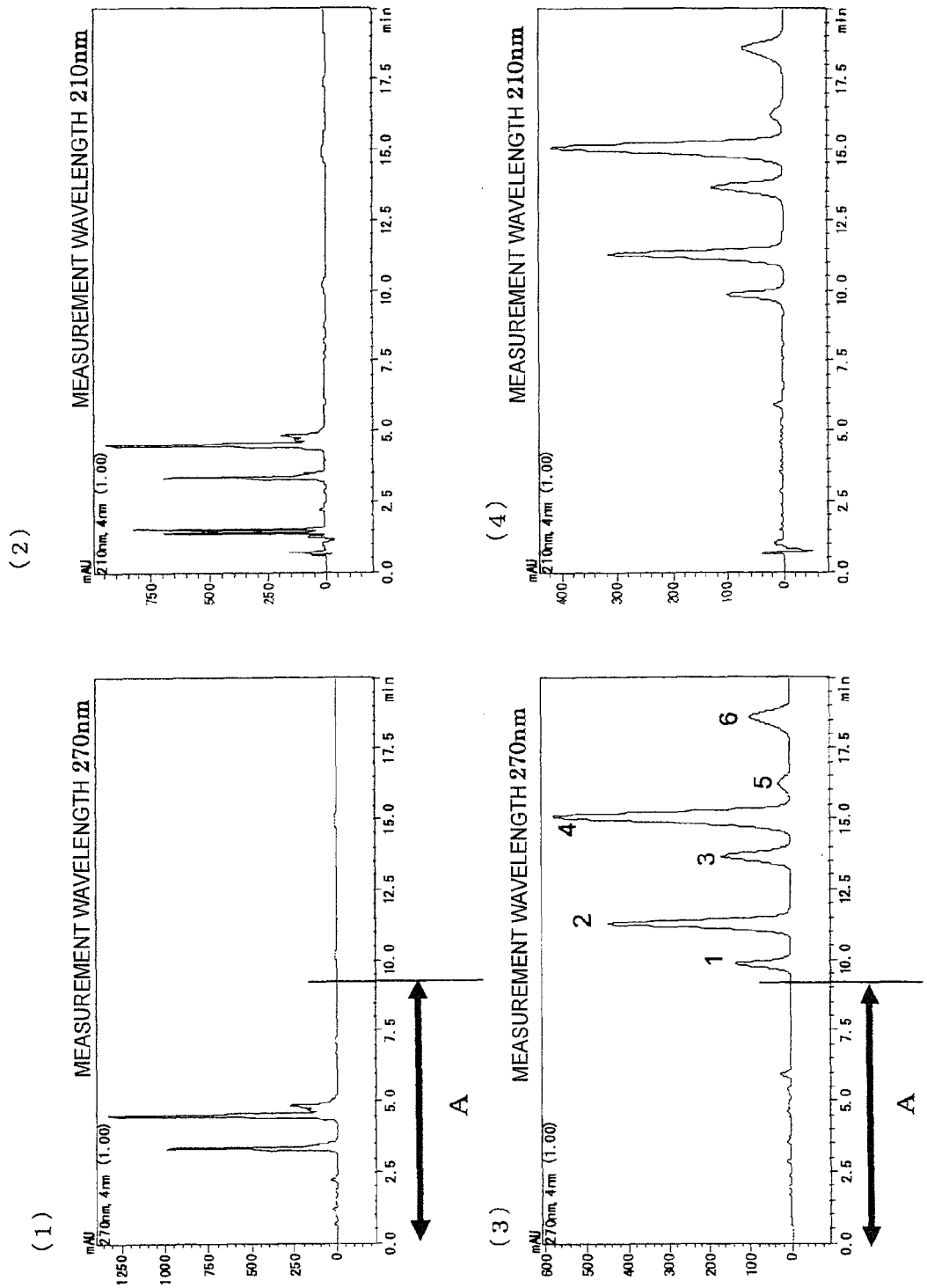
FIG. 1 is a diagram showing HPLC charts ((1) and (2)) of a decomposition product (Example 1) after a strong alkali-thermal decomposition treatment and HPLC charts ((3) and (4)) of an isomerized hop extract without the strong alkali-thermal decomposition treatment.

An "alkaline decomposition product of a hop extract" provided by the present invention (hereinafter, also simply referred to as a "decomposition product according to the present invention") can be obtained by subjecting a hop extract to an alkaline decomposition treatment. In the present invention, the "alkaline decomposition treatment" means a decomposition treatment under alkaline conditions. The "alkaline decomposition treatment" is not particularly limited as long as pH during the decomposition treatment is kept at alkaline pH. The decomposition treatment can be performed preferably at pH 9 or higher, more preferably under strong alkaline conditions, i.e., under conditions of pH 13 or higher, from the viewpoint of decomposition efficiency. An approach for the alkaline decomposition treatment will be described later. Moreover, in the present invention, the "hop extract" means an extract from hop cones and means to include an isomerized hop extract obtained by subjecting hop extract to an isomerization treatment. An extraction approach for the hop extract or the isomerization treatment will be described later.

The hop extract contains acidic resin components such as alpha acid (humulone compounds) and beta acid (lupulone compounds). Moreover, the isomerized hop extract contains acidic resin components such as iso-alpha acid (isohumulone compounds). In the present invention, the "humulone compounds" mean to include humulone, adhumulone, cohumulone, posthumulone, and prehumulone. Moreover, in the present invention, the "lupulone compounds" mean to include lupulone, adlupulone, colupulone, postlupulone, and prelupulone. Furthermore, in the present invention, the "isohumulone compounds" mean to include isohumulone, isoadhumulone, isocohumulone, isoposthumulone, isoprehumulone, tetrahydroisohumulone, tetrahydroisoadhumulone, tetrahydroisocohumulone, tetrahydroisoprehumulone, and tetrahydroisoposthumulone. The isohumulone compounds have cis- and trans-stereoisomers and mean to include both of them, unless otherwise specified.

According to Examples described later, the content of alpha acid and iso-alpha acid is reduced by subjecting the hop extract to the alkaline decomposition treatment, while the content of the other components is thereby increased. Thus, examples of the "alkaline decomposition product of the hop extract" include one in which a ratio of areas of iso-alpha acid and alpha acid to the total HPLC peak area of components other than beta acid in the decomposition product is 70% or less, preferably 30% or less, more preferably 10% or less, in carrying out HPLC analysis shown in Example 3.

Components other than alpha acid, beta acid, and iso-alpha acid contained in the decomposition product according to the present invention are compounds having lower hydrophobicity than that of the iso-alpha acid. The presence thereof can be detected easily by well known analysis means such as HPLC. For example, an alkaline decomposition product prepared by procedures described in Example 1 contains alpha acid, beta acid, and iso-alpha acid as well as compounds having lower hydrophobicity than that of these acids. A fraction containing such low hydrophobic compounds (portion shown by arrow "A" in FIG. 1; hereinafter, referred to as a low hydrophobic compound group) has physiological activities, as shown in Examples 13 and 14. Thus, examples of the decomposition product according to the present invention include one in which a ratio of areas of components other than iso-alpha acid and alpha acid to the total HPLC peak area of components other than beta acid in the decomposition product is 30% or more, preferably 70% or more, more preferably 90% or more, in carrying out HPLC analysis shown in Example 3.

Main components in the low hydrophobic compound group exhibiting physiological activities were considered to be humulinic acids from their molecular weights. In the decomposition product according to the present invention, a content of the humulinic acids contained in the decomposition product is, preferably, equal to or larger than the total content of iso-alpha acid and alpha acid in terms of the mass of substance. In the present invention, the "humulinic acids" mean to include various homologues such as humulinic acid, adhumulinic acid, cohumulinic acid, posthumulinic acid, and prehumulinic acid, and acetylhumulinic acid, dihydrohumulinic acid, acetyldihydrohumulinic acid, humulinic acid C, humulinic acid D, O-methylhumulinic acid D, oxyhumulinic acid, dehydrohumulinic acid, dehydrated humulinic acid, and dehydrated dihydrohumulinic acid. Those having cis- and trans-stereoisomers shall mean to include both of them, unless otherwise specified.

The decomposition product according to the present invention contains fatty acids that have been formed by the alkaline decomposition treatment. It has been demonstrated that an unpleasant smell unique to fatty acids may impair ingestion, depending on alkaline treatment conditions or an aspect of ingestion. Thus, for the decomposition product according to the present invention, preferably, a fatty acid has been removed from components contained in the decomposition product. More preferably, the decomposition product according to the present invention consists of, as components contained in the decomposition product, a component that forms a complex with a metal ion. In this case, a content of the fatty acid in the decomposition product according to the present invention is preferably 40% by weight or less, more preferably 10% by weight or less, of a content of the humulinic acids. An approach of removing fatty acids will be described later.

[Preparation of Alkaline Decomposition Product]
Decomposition Treatment

The decomposition product according to the present invention can be produced by subjecting an isomerized hop extract to a decomposition treatment under alkaline conditions.

Specifically, a hop extract can be heated at room temperature to a temperature of 100° C. for several seconds to 72 hours under alkaline conditions, preferably at pH 10 to 14 in a temperature range of 50° C. to 90° C. for 5 minutes to 24 hours, to thereby obtain an alkaline decomposition product of the hop extract. An alkaline aqueous solution generally used can be used for making the reaction solution alkaline. For example, an isomerized hop extract may be added at 3 to 30 w/v % in terms of the dry weight of the extract to an aqueous sodium hydroxide solution or an aqueous potassium carbonate solution having a concentration of 0.5 to 2 M.

Alpha acid such as humulone and iso-alpha acid such as isohumulone contained in the hop extract are decomposed by the alkaline decomposition treatment. The degree of decomposition of these components can be confirmed by HPLC analysis or the like.

The isomerized hop extract subjected to the decomposition treatment under alkaline conditions can be obtained by subjecting a hop extract to an isomerization treatment. A method for the isomerization treatment is known in the art, and any method may be used. Typically, the isomerization treatment can be carried out by heating a hop extract under weak alkaline conditions of pH 8 to 9 or in the presence of magnesium oxide. The hop extract may be subjected directly to the isomerization treatment. Alternatively, prior to the isomerization treatment, the hop extract is added to heated alkaline water (pH 8 to 9 after the addition of the hop extract). Dissolved alpha acid is separated from insoluble beta acid, and the obtained alpha acid fraction may be subjected to the isomerization treatment.

The hop extract subjected to the isomerization treatment can be prepared for use by subjecting, for example, cones or a compressed material thereof to extraction operation, either directly or after pulverization. The extraction method is, for example, an extraction method with an ethanol solvent or a supercritical carbon dioxide extraction method, which is used as a method for preparing a hop extract used in beer brewing. Of these methods, the supercritical carbon dioxide extraction is characterized by a few polyphenol components, more highly concentrated bitter principles and essential oil components, etc. Moreover, other methods generally used can be adopted as the hop extraction method. Examples thereof include: a method comprising dipping hop cones or a powder thereof or the like in a solvent by enfleurage, maceration, or the like; a method comprising performing extraction with stirring under heat, followed by filtration to obtain an extracted liquid; and a percolation method. The obtained extracted liquid may be used directly, depending on an aspect of use, after removal of solid matter by filtration or centrifugation as appropriate. Alternatively, the solvent is distilled off, and a portion of the residue may be concentrated or dried for use. Moreover, after the concentration or drying, the product may be further washed with a non-dissolving solvent and purified for use. Alternatively, this can also be further dissolved or suspended in an appropriate solvent for use. Furthermore, a dry product of the hop extract obtained by drying the thus-obtained solvent-extracted liquid by usual means such as drying under reduced pressure or freeze drying may be used.

Examples of the solvent used in the extraction can include water and organic solvents known in the art including: lower alcohols having 1 to 4 carbon atoms, such as methanol, ethanol, propanol, and butanol; lower alkyl esters such as ethyl acetate; glycols such as ethylene glycol, butylene glycol, propylene glycol, and glycerin; other polar solvents such as acetone and acetic acid; hydrocarbons such as benzene and hexane; and nonpolar solvents such as ethers such as ethyl ether and petroleum ether. These solvents may be used alone or can also be used in combination of two or more thereof.

In the present invention, not only the alkaline decomposition product of the isomerized hop extract but also an alkaline decomposition product of a non-isomerized hop extract can be used as the decomposition product according to the present invention. In this case, the hop extract can be heated at room temperature to a temperature of 100° C. for several seconds to 72 hours under alkaline conditions of pH 9 or higher, preferably at pH 10 to 14 in a temperature range of 50° C. to 90° C. for 5 minutes to 48 hours, to thereby obtain an alkaline decomposition product of the hop extract. For making the reaction solution alkaline, for example, the hop extract may be added at 3 to 10 w/v % in terms of the dry weight of the extract to an aqueous sodium hydroxide solution or an aqueous potassium carbonate solution having a concentration of 0.5 to 2 M. For the reaction, the hop extract may be subjected directly to the alkaline decomposition treatment. Alternatively, prior to the alkaline decomposition treatment, an alpha acid fraction may be collected from the hop extract and subjected to the decomposition treatment. The separation between alpha acid and beta acid can be carried out in the same way as above. The hop extract subjected to the decomposition treatment under alkaline conditions can be prepared by subjecting cones or a compressed material thereof to extraction operation, either directly or after pulverization, in the same way as above.

The decomposition product obtained by subjecting the hop extract to the alkaline decomposition treatment is alkaline in itself and may thus be neutralized appropriately with an acid generally used in neutralization, such as sulfuric acid, hydrochloric acid, nitric acid, phosphoric acid, citric acid, lactic acid, or tartaric acid. The neutralized decomposition product can be added, for use, to foods or pharmaceutical products as described later.

The hop extract subjected to the alkaline decomposition treatment is commercially available as a beer additive. In the present invention, such a commercially available product can be used. For example, a hop extract containing mainly humulones and lupulones extracted with supercritical carbon dioxide from a hop cone powder (e.g., CO2 Pure Resin Extract (Hopsteiner)), an extract obtained by isomerizing $CO_2$ extract of a hop cone powder (e.g., Isomerized Kettle Extract (S.S. Steiner, Inc.)), and a water-soluble extract obtained by isomerizing $CO_2$ extract of a hop cone powder and then converting it to potassium salt to prepare a low viscous liquid (e.g., ISOHOPCO2N (English Hop Products Ltd.) and Iso-Extract 30% (Hopsteiner)), can be used.

In the present invention, a hop extract prepared by extraction using a solvent adjusted to the same alkaline conditions as those in the alkaline decomposition treatment can also be used as the decomposition product according to the present invention. Specifically, cones or a compressed material thereof can be subjected, either directly or after pulverization, to extraction operation using a solvent adjusted to alkaline conditions (pH 9 or higher, preferably pH 13 or higher) to thereby prepare an alkaline decomposition product of the hop extract.

Fatty Acid Removal Treatment

The decomposition product obtained by subjecting the hop extract to the alkaline decomposition treatment contains fatty acids that are responsible for a smell. Thus, a fatty acid removal treatment for removing fatty acids that have been formed by the alkaline decomposition treatment may be carried out.

A method for removing the fatty acids is not particularly limited. For example, a method known in the art can be used, such as a method comprising subjecting the decomposition product to an acidic treatment and then removing fatty acids by volatilization with heated steam (steam distillation method), or a method comprising adsorbing fatty acids onto a carrier (adsorption method). Furthermore, in the present invention, a method comprising treating the decomposition product under acidic conditions to precipitate oil components, which are then centrifugally washed with water to thereby remove fatty acids (centrifugation method), a method comprising removing fatty acids by using microbial fermentation (fermentation method), or a method comprising collecting a component that forms a complex with a metal ion, resulting in removal of fatty acids (complex formation method), can also be used.

The complex formation method can be used for insolubilizing only physiologically active components as metal complexes, which then enable solid-liquid separation from a solution containing fatty acids. Specifically, this method is exceedingly convenient and efficient. In addition, the method is very advantageous in that operators are not exposed to the unpleasant smell of fatty acids because they work under alkaline conditions. A component obtained by adding a metal ion to the alkaline decomposition product of the hop extract, and collecting a component that has formed a complex with the metal ion may be used in the food according to the present invention or the suppression agent according to the present invention.

In the approach described above, the component that has formed a complex can be dissociated from the metal ion using an acid such as sulfuric acid, hydrochloric acid, nitric acid, phosphoric acid, citric acid, lactic acid, or tartaric acid and used in the food according to the present invention or the suppression agent according to the present invention. The metal ion that can be used in this complex formation is preferably a divalent metal ion. Examples thereof include magnesium (magnesium chloride), calcium, zinc, iron, and copper ions. Without being bound by the following theory, physiologically active components such as humulinic acids contained in the decomposition product according to the present invention are considered to be insolubilized by the formation of a complex with the metal ion.

Preparation of Alkali Metal Salt

The decomposition product according to the present invention can be allowed to form a salt with an alkali metal such as potassium or sodium to prepare an aqueous alkali metal salt solution. Moreover, the aqueous solution can be converted to a powder by spray drying or the like. Examples of the alkali metal salt that can be used in the metal salt formation of the decomposition product according to the present invention include salts whose addition to foods is acceptable, such as potassium salt and sodium salt. The potassium salt is preferable. The alkali metal salt of the decomposition product according to the present invention is excellent in water solubility and is advantageous in that it can be added easily to foods (particularly, drinks).

The thus-obtained alkali metal salt of the decomposition product according to the present invention may be subjected to the fatty acid removal treatment to remove fatty acids. Moreover, the alkali metal salt of the decomposition product according to the present invention may be prepared using the decomposition product according to the present invention subjected to the fatty acid removal treatment.

Extraction of Humulinic Acids

The alkaline decomposition product thus obtained contains humulinic acids. These humulinic acids may be isolated/purified by a further extraction step. For example, the alkaline decomposition product is adsorbed onto an adsorptive resin or the like. Then, only humulinic acids may be eluted selectively and added to foods. Alternatively, the humulinic acids may be used as the food additive according to the present invention or the suppression agent according to the present invention.

[Use of Alkaline Decomposition Product]

As shown below in Examples 13 to 15, the alkaline decomposition product of the hop extract significantly suppressed weight gain in high-fat diet-fed mice and significantly decreased the visceral and subcutaneous fats of high-fat diet-fed mice. Moreover, the alkaline decomposition product of the hop extract significantly suppressed fat accumulation in the mouse liver.

Thus, the decomposition product according to the present invention is useful as an agent for suppressing fat accumulation (particularly, an agent for suppressing visceral fat and subcutaneous fat accumulation) and an agent for suppressing weight gain. Moreover, the decomposition product according to the present invention is useful in the prevention and/or treatment of obesity.

Moreover, the alkaline decomposition product of the hop extract used in Examples contains low-molecular-weight compounds typified by humulinic acids (Examples 3, 4, 5, and 12). Thus, the humulinic acids are useful as an agent for suppressing fat accumulation and an agent for suppressing weight gain. Moreover, the humulinic acids are useful in the prevention and/or treatment of obesity.

The decomposition product according to the present invention or the humulinic acids are free from strong bitterness as produced by the isomerized hop extract (Examples 11, 16, and 17). Thus, the decomposition product according to the present invention or the humulinic acids are advantageous in that they can be used directly in foods and drinks or pharmaceutical products without taking the means of masking bitterness, while the physiological activities or effects as described above can be expected.

[Pharmaceutical Product and Food]

When the decomposition product according to the present invention is provided as a pharmaceutical product, the pharmaceutical product can be produced by mixing the decomposition product according to the present invention with pharmaceutically acceptable additives. The decomposition product according to the present invention is free from strong bitterness as produced by isohumulone compounds and is thus advantageous in that a preparation expected to have the predetermined efficacy can be obtained without taking the means of masking bitterness or with bitterness sufficiently masked using existing masking means.

In the present invention, not only the alkaline decomposition product of the hop extract itself but also, as components contained in the decomposition product, a component that forms a complex with a metal ion or isolated/purified humulinic acids can be used. In the component that forms a complex with a metal ion, the majority of fatty acids formed by alkaline decomposition have been removed. Thus, this component is advantageous in that the component, even when used at a high concentration in a pharmaceutical product, does not cause an unpleasant smell unique to fatty acids.

The decomposition product according to the present invention can be administered orally or parenterally as an active ingredient. The oral administration is preferable. Examples of oral preparations include granules, powders, tablets (including sugar-coated tablets), pills, capsules, syrups, emulsions, and suspensions. Examples of parenteral preparations include injections (e.g., subcutaneous, intravenous, intramuscular, and intraperitoneal injections), drip infusions, preparations for external use (e.g., transnasally administrable preparations, percutaneous preparations, and ointments), and suppositories (e.g., rectal suppositories and vaginal suppositories). These preparations can be formulated by an approach usually performed in the art using pharmaceutically acceptable carriers. Examples of the pharmaceutically acceptable carriers include excipients, binders, diluents, additives, flavors, buffers, thickeners, coloring agents, stabilizers, emulsifying agents, dispersants, suspending agents, and preservatives. For example, magnesium carbonate, magnesium stearate, talc, sugar, lactose, pectin, dextrin, starch, gelatin, tragacanth, methylcellulose, sodium carboxymethylcellulose, low-melting-point wax, and cocoa butter can be used as the carriers.

The preparations can be produced, for example, as follows.

The oral preparations can be produced by adding, for example, an excipient (e.g., lactose, saccharose, starch, and mannitol), a disintegrant (e.g., calcium carbonate and carboxymethylcellulose calcium), a binder (e.g., gelatinized starch, gum arabic, carboxymethylcellulose, polyvinylpyrrolidone, and hydroxypropylcellulose), or a lubricant (e.g., talc, magnesium stearate and polyethylene glycol 6000) to the active ingredient, compression-molding the mixture, and subsequently coating the agents, if necessary by a method known per se in the art for the purpose of masking of tastes, enteric coating, or sustained release. For example, ethylcellulose, hydroxymethylcellulose, polyoxyethylene glycol, cellulose acetate phthalate, hydroxypropylmethylcellulose phthalate, and EUDRAGIT (manufactured by Rohm Pharma, Germany; methacrylic acid-acrylic acid copolymer) can be used as a coating agent.

The injections can be produced by dissolving, suspending, or emulsifying the active ingredient together with a dispersant (e.g., Tween 80 (manufactured by Atlas Powder Company, USA), HCO60 (manufactured by NIKKO CHEMICALS CO., LTD.), polyethylene glycol, carboxymethylcellulose, sodium alginate, and the like), a preservative (e.g., methylparaben, propylparaben, benzyl alcohol, chlorobutanol, and phenol), a tonicity agent (e.g., sodium chloride, glycerin, sorbitol, glucose, and invert sugar), and the like in an aqueous solvent (e.g., distilled water, saline, and Ringer's solution, etc.) or an oily solvent (e.g., plant oils such as olive oil, sesame oil, cottonseed oil, and corn oil, and propylene glycol) or the like. In this procedure, additives such as a solubilizer (e.g., sodium salicylate and sodium acetate), a stabilizer (e.g., human serum albumin), or a soothing agent (e.g., benzalkonium chloride and procaine hydrochloride) may be added thereto, if desired.

The preparations for external use can be produced by preparing the active ingredient into compositions in a solid, semisolid, or liquid state. For example, the compositions in a solid state can be produced by pulverizing the active ingredient either directly or after adding and mixing of an excipient (e.g., lactose, mannitol, starch, microcrystalline cellulose, and saccharose), a thickener (e.g., natural gums, cellulose derivatives, and acrylic acid polymers), and the like. The compositions in a liquid state can be produced in almost the same way as in the injections. The compositions in a semisolid state are preferably aqueous or oily gels or ointment forms. Moreover, all of these compositions may contain a pH adjuster (e.g., carbonic acid, phosphoric acid, citric acid, hydrochloric acid, and sodium hydroxide), a preservative (e.g., p-hydroxybenzoate esters, chlorobutanol, and benzalkonium chloride), and the like. The suppositories can be produced by preparing the active ingredient into compositions in an oily or aqueous solid, semisolid, or liquid state. Examples of an oily base used in the compositions include glycerides of higher fatty acids [e.g., cocoa butter and Witepsols (manufactured by Nobel Dynamite Companies)], intermediate fatty acids [e.g., Miglyols (manufactured by Nobel Dynamite Companies)], and plant oils (e.g., sesame oil, soybean oil, and cottonseed oil). Examples of an aqueous base include polyethylene glycols and propylene glycol. Moreover, examples of an aqueous gel base include natural gums, cellulose derivatives, vinyl polymers, and acrylic acid polymers.

The food additive according to the present invention is the decomposition product according to the present invention intended to be added to foods. The decomposition product according to the present invention exhibits physiological effects such as fat accumulation suppression effect and weight gain suppression effect, as described above. Thus, the food additive according to the present invention also includes those intended to be added to foods expected to have the physiological effects of the decomposition product according to the present invention. A target or aspect of addition can follow the description about the food according to the present invention.

The food according to the present invention is a food or drink containing an effective amount of the decomposition product according to the present invention. In this context, the phrase "containing an effective amount" of the decomposition product according to the present invention means that humulinic acids are ingested in the range of the amount described below when individual foods and drinks are ingested in an ordinary amount.

When the decomposition product according to the present invention is provided as a food, the decomposition product according to the present invention can be mixed directly into the food. More specifically, the food according to the present invention may be a food or drink directly prepared from the decomposition product according to the present invention, a food or drink further containing various proteins, sugars, fat, a trace element, vitamins, etc., a food or drink in a liquid, semiliquid, or solid state, a food or drink in an aqueous solution of potassium salt, sodium salt, etc., or a general food or drink supplemented with the decomposition product according to the present invention. The decomposition product according to the present invention is free from strong bitterness as produced by isohumulone compounds and is thus advantageous in that a food expected to have the predetermined physiological effects can be obtained without taking the means of masking bitterness or with bitterness sufficiently masked using existing masking means.

In the present invention, not only the alkaline decomposition product of the hop extract itself but also, as components contained in the decomposition product, a component that forms a complex with a metal ion or isolated/purified humulinic acids can be used in a food. In the component that forms a complex with a metal ion, the majority of fatty acids formed by alkaline decomposition have been removed. Thus, this component is advantageous in that the component, even when used at a high concentration in a food, does not cause an unpleasant smell unique to fatty acids.

In the present invention, the "food" means to include health foods, functional foods, foods for specified health use, and foods for patients.

Moreover, the form of the "food" is not particularly limited. For example, a drink form may be used.

The decomposition product according to the present invention has fat accumulation suppression effect and weight gain suppression effect and can thus be provided as a food with health-maintaining or promoting benefits, specifically, a food having both the functions of fat accumulation suppression effect and weight gain suppression effect, by mixing the decomposition product according to the present invention into a daily ingested food or a healthy or functional food ingested as a supplement, preferably, a lipid-containing food, a high-calorie food, etc. Specifically, the food according to the present invention can be provided as a food suitable for consumers who are concerned about fat accumulation (particularly, the accumulation of body and visceral fats) or consumers who are concerned about a weight gain, particularly as a food for specified health use.

Specific examples of such foods and drinks can include, but not limited to: carbohydrate-containing foods and drinks such as steamed rice dishes, noodles, bread dishes, and pasta dishes; various kinds of sweets such as western confectionery (e.g., cookies and cake), Japanese confectionery (e.g., manju (steamed bean-jam bun) and yohkan (azuki bean jelly)), candies, chewing gums, and cold desserts (yogurt and pudding) or frozen desserts; alcoholic drinks such as whiskey, bourbon, spirits, liqueur, wine, fruit wine, sake, Chinese liquor, shochu (distilled spirits), beer, nonalcoholic beer having an alcohol content of 1% or lower, sparkling liquors, other miscellaneous liquors, and chuhai (Japanese highball based on distilled spirits); nonalcoholic drinks such as fruit juice-containing drinks, vegetable juice-containing drinks, drinks containing fruit juice and vegetable juice, soft drinks, milk, soybean milk, dairy drinks, drink-type yogurt, drink-type jelly, coffee, cocoa, tea drinks, energy drinks, sports drinks, and mineral water; processed products obtained using eggs and processed products (including food delicacies) of seafood (squid, octopus, seashell, eel, and the like) or meats (including plucks such as liver).

Examples of the tea drinks include black tea, green tea, barley tea, brown rice tea, sencha (green tea of middle grade), gyokuro (high-quality green tea), hojicha (roasted green tea), oolong tea, turmeric tea, pu-erh tea, rooibos tea, rose tea, chrysanthemum tea, and herb tea (e.g., mint tea and jasmine tea).

Examples of fruits used in the fruit juice-containing drinks or the drinks containing fruit juice and vegetable juice include apples, Japanese mandarin, grapes, bananas, pears, and Japanese plums. Moreover, examples of vegetables used in the vegetable juice-containing drinks or the drinks containing fruit juice and vegetable juice include tomatoes, carrots, celery, cucumbers, and watermelons.

The pharmaceutical product and the food according to the present invention are low toxic and are used with safety for mammals (e.g., humans, mice, rats, rabbits, dogs, cats, cattle, horses, pigs, monkeys, etc.) in need thereof because the hop extract, which has been ingested as foods and drinks for long years by human beings, is used therein. The dose or intake of the decomposition product according to the present invention can be determined depending on a recipient, the age and body weight of the recipient, symptoms, an administration period, a dosage form, an administration method, a combination of drugs, etc. For example, the decomposition product according to the present invention, when administered as a pharmaceutical product, can be administered to an adult (body weight: 60 kg) orally in a daily dose range of 10 to 600 mg, preferably 20 to 200 mg, or parenterally in a daily dose range of 1 to 100 mg, preferably 3 to 30 mg, in terms of humulinic acids, which can be administered in one portion to three divided portions per day. Drugs having the mechanism of different action to be used in combination with the decomposition product according to the present invention can also be determined appropriately based on the respective doses clinically used. Moreover, when the decomposition product according to the present invention is ingested as a food, the decomposition product according to the present invention can be mixed into the food such that the daily intake in adult (body weight: 60 kg) is in a range of 25 to 9600 mg, preferably in a range of 25 to 780 mg, in terms of humulinic acids.

EXAMPLES

The present invention will be described specifically with reference to examples below. However, the present invention is not limited to these examples.

Example 1

Preparation of Strong Alkali-Thermal Decomposition Product

An isomerized hop extract (Iso-Extract 30%; Hopsteiner) composed mainly of isohumulone, isoadhumulone, and isocohumulone was added at 3 w/v % in terms of the dry weight of the extract into a 2 M aqueous sodium hydroxide solution heated to 95° C., and the heating was maintained at 95° C. for 10 minutes. pH in the aqueous solution during heating was 13 or higher.

Example 2

Preparation of Weak Alkali-Thermal Decomposition Product

An isomerized hop extract (Iso-Extract 30%; Hopsteiner) composed mainly of isohumulone, isoadhumulone, and isocohumulone was added at 6 w/v % in terms of the dry weight of the extract into a 0.5 M aqueous potassium carbonate solution heated to 80° C., and the heating time was maintained until 24 hours later. pH in the aqueous solution during heating was 10 to 12.

Example 3

Analysis of Alkali-Thermal Decomposition Products

The alkali-thermal decomposition solutions prepared in Examples 1 and 2 were pretreated as follows
[Preanalysis Treatment of Reaction Solution]
Each collected reaction solution was adjusted to pH 3 or lower with hydrochloric acid and diluted with ethanol such that the HPLC sample solution contained 0.1 to 0.3 w/v % (in terms of dry weight) isomerized hop extract.
[HPLC Constituting Apparatuses]
Pump: LC-10ADvp×2 (Shimadzu Corp.)
Degasser: DGU-14A (Shimadzu Corp.)
System controller: CBM-20A (Shimadzu Corp.)
Autosampler: SIL-20AC (Shimadzu Corp.)
Column oven: CTO-20AC (Shimadzu Corp.)
Photodiode array detector: SPD-M20A (Shimadzu Corp.)
Waveform analyzing software: LCSolution (Shimadzu Corp.)
[HPLC Conditions]
Column: Alltima C18 4.6 mm I.D.×150 mm, particle size of 5 μm
Flow rate: 1.8 mL/min
Elution solvent "A": water/phosphoric acid, 1000/0.2, (v/v)+ EDTA (free) 0.02% (w/v)
Elution solvent "B": acetonitrile
Injection amount: 10 μL
Column temperature: 40° C.
Detection wavelength: 270 nm (humulinic acids, iso-alpha acid, alpha acid, beta acid)
210 nm (fatty acids)
Gradient program (i): 0-20 min: 52% "B" isocratic
20-30 min: 52-70% "B" linear gradient
30-60 min: 70% "B" isocratic
60 min: stop
When alkali-thermal decomposition is performed using an isomerized hop extract that is composed mainly of isohumulone, isoadhumulone, and isocohumulone and has ignorable contents of alpha acids and beta acids, assay based on the following gradient program (ii) is also possible.
Gradient program (ii): 0-20 min: 52% "B" isocratic
20 min:stop The ratio (%) of peak area values of isohumulone compounds and humulone compounds in the total area value (mAU·min) of all peaks except for beta acid detected at a detection wavelength of 270 nm under the analysis conditions described above was calculated. In this context, all peaks except for beta acid are defined as peaks detected in regions obtained until after adhumulone elution in the case of using the gradient program (i) and in regions obtained until after cis-isoadhumulone elution in the case of using the gradient program (ii). In the description below, the term "all peaks" shall follow this definition. For waveform analysis, regions in which solvent peaks or negative peaks caused by injection shock appeared were regarded as regions excluded from analysis.

FIGS. 1(1) and 1(2) show HPLC chromatograms (gradient program (ii)) during analysis of the decomposition product prepared in Example 1 described above. Moreover, FIGS. 1(3) and 1(4) show chromatograms during analysis using distilled water instead of the 2 M aqueous sodium hydroxide solution without performing heating. The isohumulone compounds thus detected were trans-isocohumulone, cis-isocohumulone, trans-isohumulone, cis-isohumulone, trans-isoadhumulone, and cis-isoadhumulone which corresponded to peaks "1" to "6", respectively, in FIG. 1(3).

Figure 2:
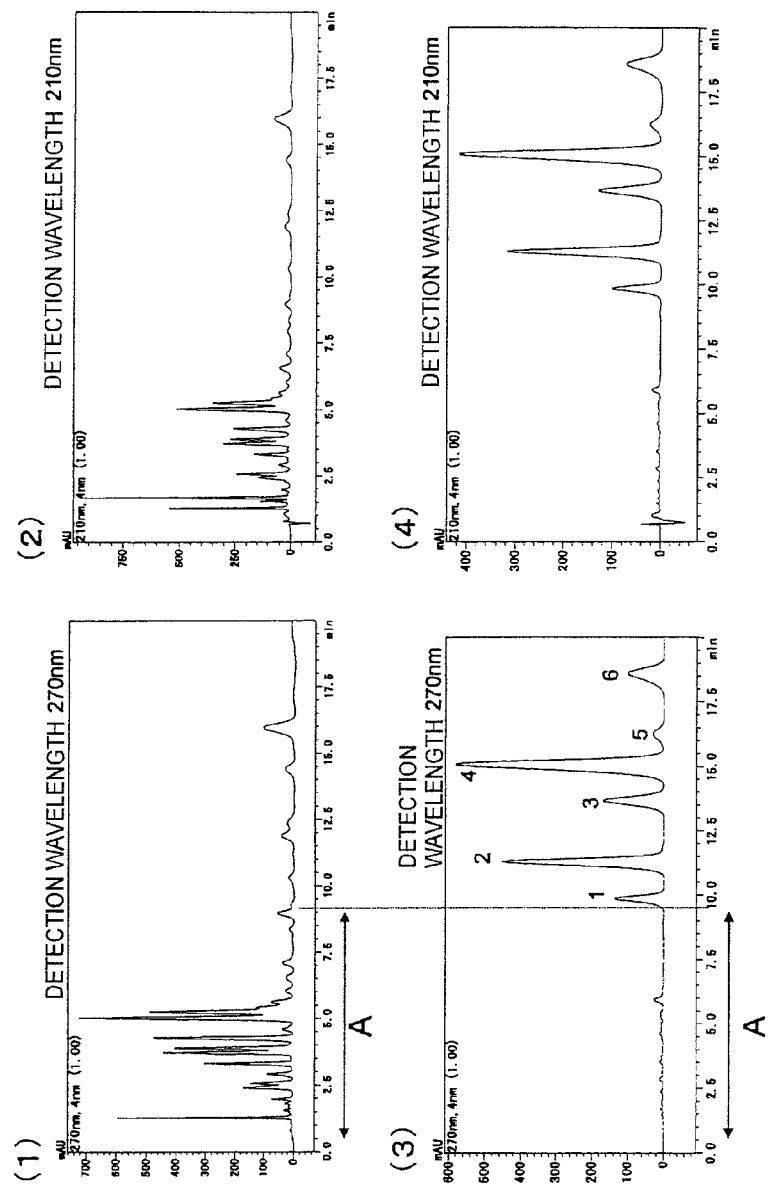
FIG. 2 is a diagram showing HPLC charts ((1) and (2)) of a decomposition product (Example 2) after a weak alkali-thermal decomposition treatment and HPLC charts ((3) and (4)) of an isomerized hop extract without the weak alkali-thermal decomposition treatment.

FIGS. 2(1) and 2(2) show HPLC chromatograms (gradient program (ii)) during analysis of the decomposition product prepared in Example 2. Moreover, FIGS. 2(3) and 2(4) show chromatograms during analysis using distilled water instead of the 0.5 M aqueous potassium carbonate solution without performing heating.

The ratio (%) of the peak area values of the isohumulone compounds in the total area value (mAU·min) of all peaks detected at a detection wavelength of 270 nm was as shown in Table 1 for each analysis sample.

TABLE 1

| Reaction solution | Heating temperature | Peak area ratio (%) (Isohumulone compound peaks/total peaks) |
|---|---|---|
| 2M sodium hydroxide | 95° C. | 0.3 |
| 0.5M potassium carbonate | 80° C. | 14.9 |
| Distilled water | Room temperature | 95.4 |

As is evident from these results, the peaks of the isohumulone compounds were considerably reduced or disappeared in the isomerized hop extract subjected to the alkali-thermal decomposition treatment.

Moreover, peaks of compounds having lower hydrophobicity than that of isohumulone compounds newly appeared in the alkali-thermal decomposition product. Specifically, peaks of fractions eluted earlier than the elution time of trans-isocohumulone (i.e., peaks in the range of a fraction shown by arrow "A" in FIGS. 1 and 2) correspond to these peaks. The ratio (%) of peak area values of the compounds having lower hydrophobicity than that of isohumulone compounds in the total area value (mAU·min) of all peaks detected at a detection wavelength of 270 nm was as shown in Table 2.

TABLE 2

| Reaction solution | Heating temperature | Peak area ratio (%) (peaks of compounds having lower hydrophobicity than that of isohumulone/total peaks) |
|---|---|---|
| 2M sodium hydroxide | 95° C. | 99.7 |
| 0.5M potassium carbonate | 80° C. | 81.7 |
| Distilled water | Room temperature | 4.6 |

Figure 3:
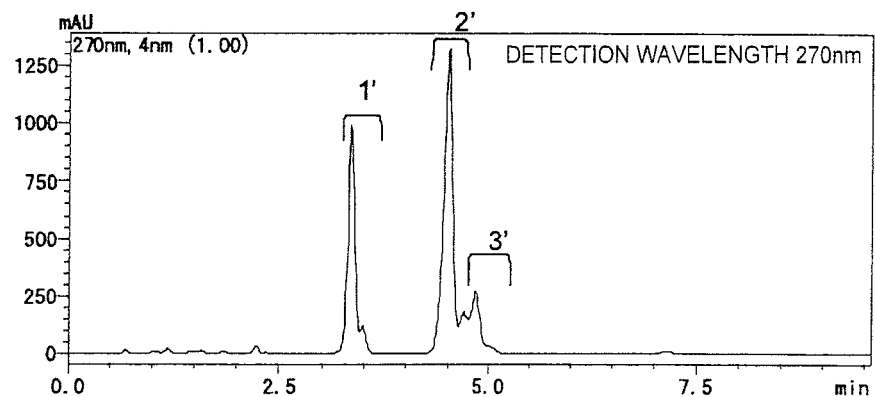
FIG. 3 is an enlarged view of the HPLC charts of FIGS. 1(1) and 1(2).
Figure 3:
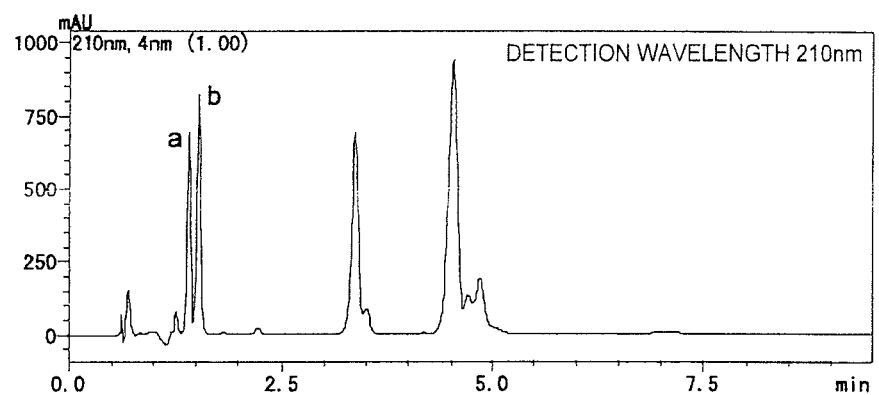

FIG. 3 shows an enlarged view of an HPLC chromatogram at elution times of the compounds having lower hydrophobicity than that of isohumulone compounds after the strong alkali-thermal decomposition treatment. It is known that in the alkali-heat treatment of the isohumulone compounds, the side-chain acyl group at position C4 is hydrolyzed to form humulinic acids and fatty acids (4-methyl-2-pentenoic acid and 4-methyl-3-pentenoic acid, and the like). Peaks "a" and "b" detected at 210 nm were presumed to be fatty acids formed by decomposition. The compound of the peak "b" agreed with 4-methyl-2-pentenoic acid available as a commercially available preparation in terms of retention time and molecular weight and was thus identified as 4-methyl-2-pentenoic acid. Moreover, as a result of LC-MS analysis, the compound of the peak "a" had the same molecular weight as that of the peak "b" and was identified as 4-methyl-3-pentenoic acid from results of NMR measurement after collection of the fraction. Peaks "1", "2", and "3" observed at 270 nm were identified as cohumulinic acid, humulinic acid, and adhumulinic acid, respectively (each of which was a mixture of cis and trans forms), as a result of various instrumental analyses.

Figure 4:
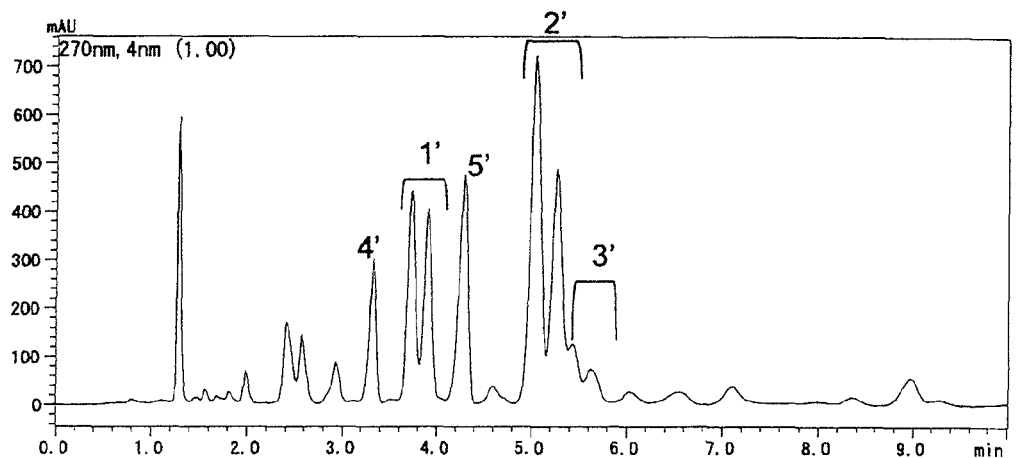
FIG. 4 is an enlarged view of the HPLC charts of FIGS. 2(1) and 2(2).
Figure 4:
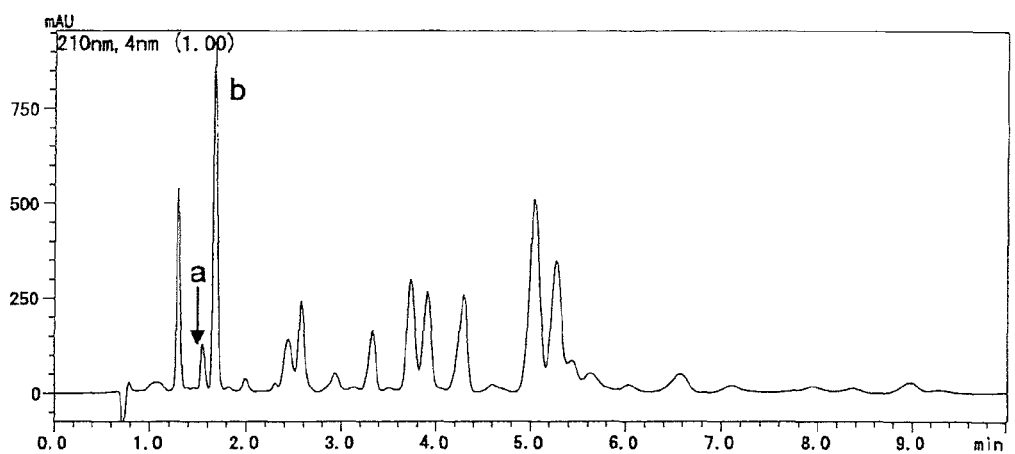

FIG. 4 shows an enlarged view of an HPLC chromatogram at elution times of the compounds having lower hydrophobicity than that of isohumulone compounds after the weak alkali-thermal decomposition treatment. As in the strong alkali-thermal decomposition product, peaks "1", "2", and "3" were detected at 270 nm. In addition, peaks "4" and "5" that were identified as mixtures of acetylhumulinic acid homologues (humulinic acid derivatives) as a result of instrumental analysis were detected.

In the analysis method described above, alpha acid, iso-alpha acid, humulinic acids, and fatty acids contained in the hop extract or an alkaline decomposition product thereof can be quantitatively analyzed. For example, Internal Calibration Standards ICE-2, ICS-12, ICS-T2, and the like available from American Society of Brewing Chemists (ASBC) can be used as standards for quantitative analysis for alpha acid or iso-alpha acid. Moreover, the humulinic acids can be quantified with trans-humulinic acid as a standard. The trans-humulinic acid can be isolated by an approach known in the art and used in quantification. Moreover, the 4-methyl-2-pentenoic acid can be quantified with a commercially available preparation or an isolate obtained by an approach known in the art as a standard. The 4-methyl-3-pentenoic acid can be quantified using, as a standard, a fraction collected and purified by HPLC from the alkaline decomposition product as well as an isolate obtained by an approach known in the art.

Example 4

Removal of Fatty Acids (1) (Complex Formation Method)

The alkali-thermal decomposition products prepared in Examples 1 and 2 contained fatty acids attributed to the decomposition reaction. Depending on an aspect of ingestion, pleasant ingestion seemed difficult due to an unpleasant smell attributed to these fatty acids. Thus, the removal of the fatty acids was discussed.

Sulfuric acid was added to 22 L of the decomposition product obtained in Example 1, and the solution was adjusted to approximately pH 9. Then, 1.6 L of a 2 M magnesium chloride solution was added thereto to obtain a white cloudy solution containing a complex with magnesium.

Subsequently, a white filtration residue was obtained by filtration, and this residue was washed with 1 M magnesium chloride and 0.5 M sodium bicarbonate solutions and washed with 2 M sulfuric acid for the purpose of dissociating the complex therefrom, to thereby obtain 270 g of yellow solid matter.

Figure 5:
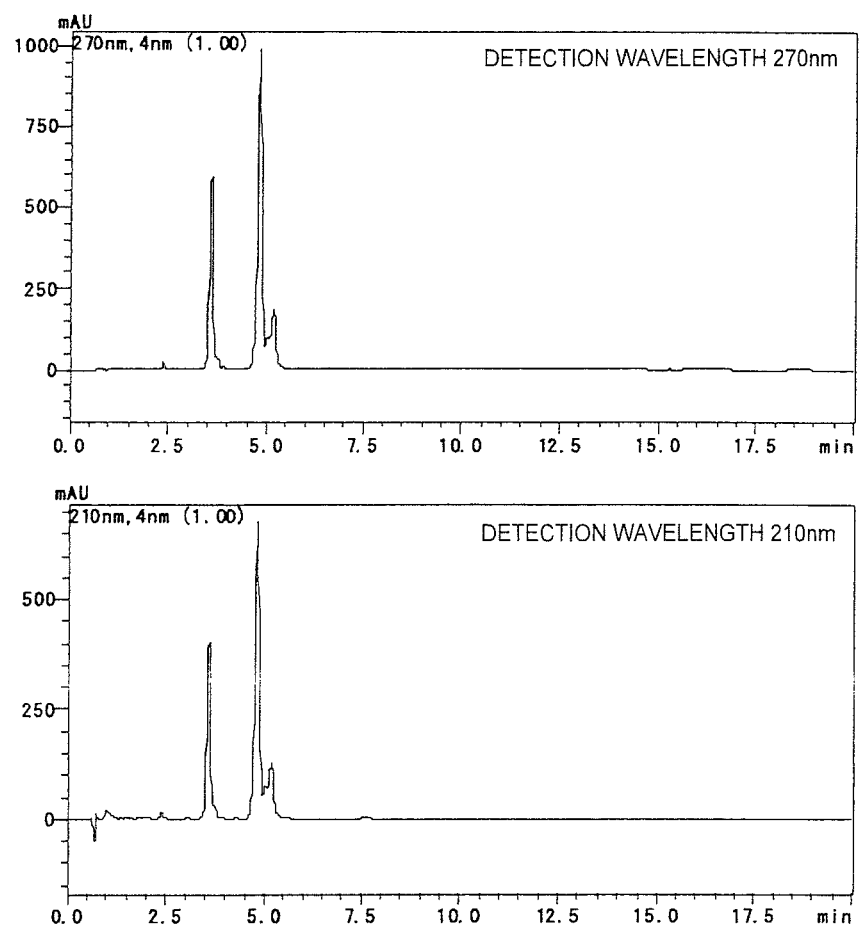
FIG. 5 is a diagram showing HPLC charts of a sample of a fatty acid-removed decomposition product (Example 4) according to the present invention used in physiological effect evaluation in animals (Example 14).

The yellow solid matter was dissolved in ethanol. Fatty acids at a measurement wavelength of 210 nm and humulinic acids at a measurement wavelength of 270 nm were quantitatively analyzed by the same approach as in Example 3. The rate at which fatty acids were removed is shown in Table 3 as change in the ratio (%) of the weight of fatty acids to that of humulinic acids in the decomposition product. Moreover, a chromatogram during analysis is shown in FIG. 5.

TABLE 3

| | Weight of fatty acids (%) with respect to weight of humulinic acids contained in decomposition product |
|---|---|
| Before fatty acid removal | 31.7 |
| After fatty acid removal | 0.00 |

The fatty acid peaks disappeared, demonstrating that fatty acids can be removed favorably.

Example 5

Removal of Fatty Acids (2) (Complex Formation Method)

The removal of fatty acids by the complex formation method from the product obtained in Example 2 was discussed. This removal was performed according to the method described in Example 4.

Figure 6:
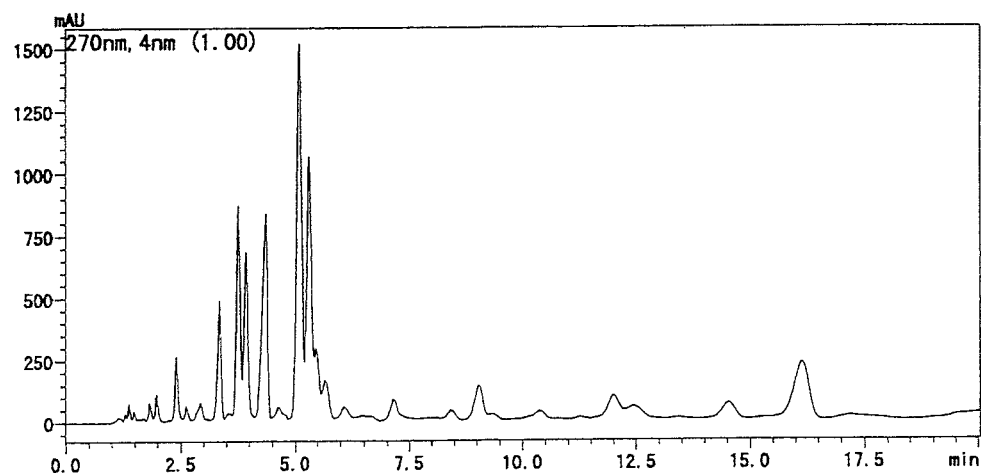
FIG. 6 is a diagram showing HPLC charts of a sample of a fatty acid-removed decomposition product (Example 5) according to the present invention.
Figure 6:
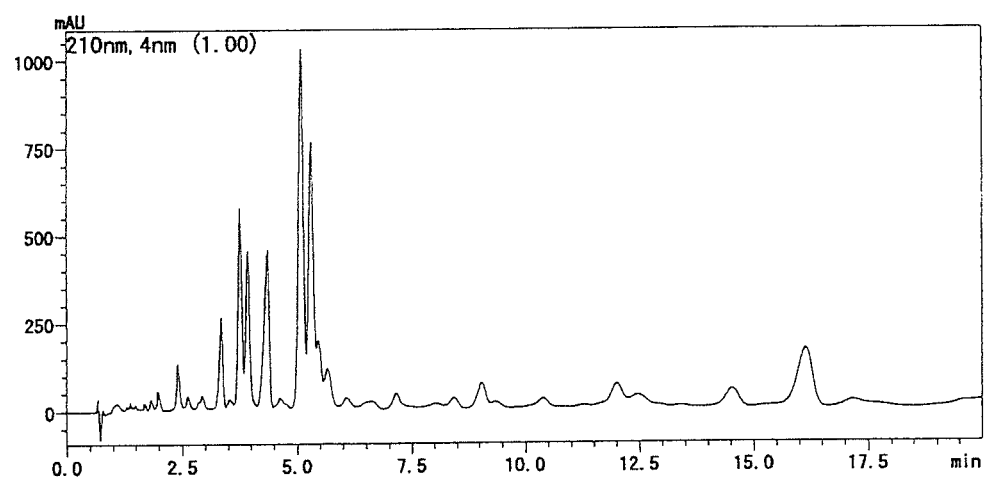

The obtained yellow solid matter was dissolved in ethanol. Fatty acids at a measurement wavelength of 210 nm and humulinic acids at a measurement wavelength of 270 nm were quantitatively analyzed by the same approach as in Example 3. The rate at which fatty acids were removed is shown in Table 4 as change in the ratio (%) of the weight of fatty acids to that of humulinic acids in the decomposition product. Moreover, a chromatogram during analysis is shown in FIG. 6.

TABLE 4

| | Weight of fatty acids (%) with respect to weight of humulinic acids contained in decomposition product |
|---|---|
| Before fatty acid removal | 12.3 |
| After fatty acid removal | 0 |

The fatty acid peaks disappeared, demonstrating that fatty acids can be removed favorably.

Example 6

Removal of Fatty Acids (1) (Centrifugation Method)

The removal of fatty acids by centrifugation from the product obtained in Example 1 was discussed.

The solution was adjusted to approximately pH 2 by the addition of sulfuric acid to the product and centrifuged (5000 rpm, 10 min) to obtain a yellowish brown solid matter. The solid matter was further washed with a 0.5 M sodium bicarbonate solution and then dissolved in ethanol. Humulinic acids and fatty acids contained in the resin were analyzed by the method described in Example 3.

The rate at which fatty acids were removed by centrifugation is shown in Table 5 as change in the ratio (%) of the weight of fatty acids to that of humulinic acids in the decomposition product.

TABLE 5

| | Weight of fatty acids (%) with respect to weight of fumulinic acids contained in decomposition product |
|---|---|
| Before fatty acid removal | 36.8 |
| After fatty acid removal | 12.3 |

It was demonstrated that fatty acids can be removed favorably by centrifugation.

Example 7

Removal of Fatty Acids (2) (Centrifugation Method)

The removal of fatty acids by centrifugation from the product obtained in Example 2 was discussed.

A yellowish brown solid matter was obtained according to the method described in Example 6. The obtained solid matter was dissolved in ethanol. Then, humulinic acids and fatty acids were analyzed by the method described in Example 3.

The rate at which fatty acids were removed by centrifugation is shown in Table 6 as change in the ratio (%) of the weight of fatty acids to that of humulinic acids in the decomposition product.

TABLE 6

| | Weight of fatty acids (%) with respect to weight of fumulinic acids contained in decomposition product |
|---|---|
| Before fatty acid removal | 12.3 |
| After fatty acid removal | 5.16 |

It was demonstrated that fatty acids can be removed favorably by centrifugation.

Example 8

Removal of Fatty Acids (Evaluation of Assimilation of Fatty Acids by Microorganisms)

Fatty acids in the product obtained in Example 1 were examined for assimilability by microorganisms.

*Aspergillus oryzae* RIB40 (NBRC100959), *Aspergillus kawachii* NBRC4308, *Trichoderma reesei* NBRC31239, and *Penicillium camenberti* PC12 were used in the evaluation. Each bacterial strain was precultured. Then, 1 mL of the bacterial cells was added to 100 mL of a main culture medium. *Penicillium camenberti* PC12 was cultured at 20° C. and the other bacteria were cultured at 30° C. for 4 days under aerobic conditions.

TABLE 7

Composition of the culture mediums

| | % |
|---|---|
| Preculture medium | |
| Glucose | 0.5 |
| $K_2HPO_4$ | 0.1 |
| $MgSO_4 \cdot 7H_2O$ | 0.02 |
| $FeSO_4 \cdot 7H_2O$ | 0.001 |
| $CaCl_2$ | 0.001 |
| $(NH_4)_2SO_4$ | 0.1 |
| Yeast Extract | 0.5 |
| Main culture medium | |
| The Decomposition product in Example 1 | 0.1 |
| $K_2HPO_4$ | 0.1 |
| $MgSO_4 \cdot 7H_2O$ | 0.02 |
| $FeSO_4 \cdot 7H_2O$ | 0.001 |
| $CaCl_2$ | 0.001 |
| $(NH_4)_2SO_4$ | 0.1 |
| Yeast Extract | 0.5 |

After 0, 24, 48, 72, and 96 hours into the culture, 500 μL of each culture solution was sampled and centrifuged at 6000 rpm at room temperature. To 100 μL. of the obtained supernatant, 80 μL of ethanol and 20 μL of 2 M aqueous HCl were added, and the mixture was well stirred to prepare sample solutions for HPLC. A quantitative analysis method in HPLC is as described above.

As a result of HPLC analysis, the ratio (%) of the weight of fatty acids to that of humulinic acids in each obtained culture medium was used as an index for the assimilability of fatty acids.

Figure 7:
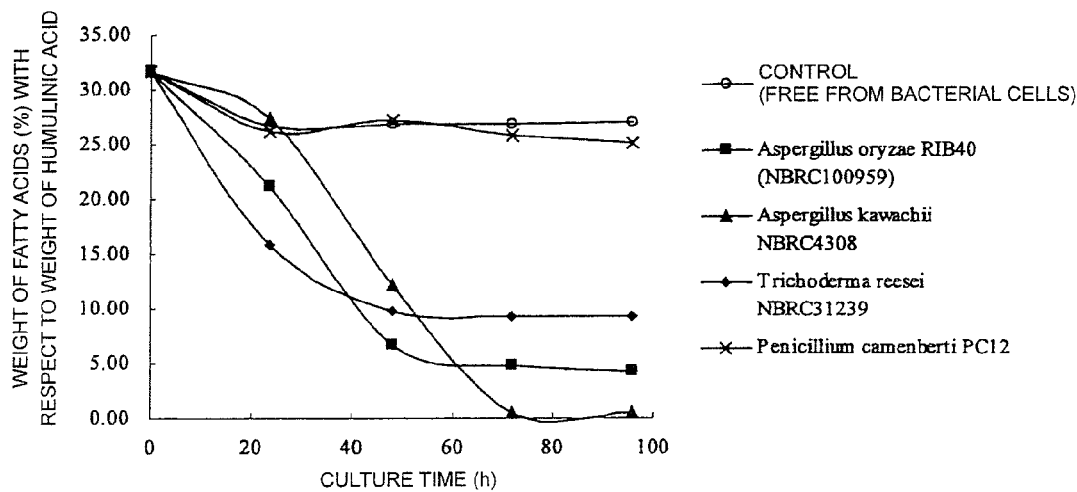
FIG. 7 is a diagram showing the rate at which fatty acids contained in the decomposition product according to the present invention were removed by microbial fermentation.

FIG. 7 shows time-dependent change in the index for the assimilability of fatty acids by each bacterial strain.

Of the bacterial strains used, *Aspergillus oryzae* RIB40 (NBRC100959), *Aspergillus kawachii* NBRC4308, and *Trichoderma reesei* NBRC31239 were confirmed to assimilate fatty acids. Particularly, in *Aspergillus kawachii* NBRC4308, the assimilation was remarkable, and the unpleasant smell of fatty acids was also sensorily confirmed to almost completely disappear in the samples after 72 hours.

Fatty acids can be removed by any of the methods described above in Examples 4 to 8. Particularly, in Examples 4 and 5 (complex formation method), an unpleasant smell attributed to fatty acids generated during the working process was significantly reduced, and the operation is also convenient and very efficient.

Example 9

Conversion of Alkaline Decomposition Product to Potassium Salt

A 3 M aqueous potassium carbonate solution was added to the yellow solid matter obtained in Example 7, with heating to 80° C., to adjust its pH to 8 to obtain an aqueous potassium salt solution of the alkaline decomposition product. The obtained aqueous potassium salt solution was diluted and subjected to HPLC analysis according to the method of Example 3. The aqueous potassium salt solution was adjusted such that the solid content of the alkaline decomposition product was 20% (w/w).

Example 10

Sensory Evaluation of Smell

[Method for Sensory Evaluation of Smell]

The products obtained in Examples 4 to 7 and the product obtained in Example 1 (control) were evaluated for their unpleasant smells attributed to fatty acids by sensory evaluation using 7 in-house panelists by the following method: the decomposition products of Examples 1 and 4 to 7 were separately added to a citrate buffer solution (pH: approximately 3.5) such that 500 ppm humulinic acids were contained therein. The prepared solutions were subjected to the evaluation.

In the sensory evaluation, the smell of each solution was confirmed over several seconds and evaluated according to evaluation criteria. The results were determined as a mean of evaluation scores of the 7 panelists and indicated in symbols according to the following criteria:

A: very good (the mean was 0 to less than 1)
B: good (the mean was 1 or more to less than 2)
C: slightly poor (the mean was 2 or more to less than 3)
D: very poor (the mean was 3 or more to 4)

[Evaluation Criteria]

TABLE 8

| Evaluation point | Evaluation Criteria | Evaluation score |
|---|---|---|
| Smell | No unpleasant smell was felt, and a pleasant smell was felt. | 0 |
| | An unpleasant smell was slightly felt. | 1 |
| | An unpleasant smell was felt. | 2 |
| | An unpleasant smell was strongly felt. | 3 |
| | An unpleasant smell was very strongly felt. | 4 |

[Evaluation Results]

TABLE 9

| | Smell score | Evaluation results |
|---|---|---|
| Reaction solution in Example 1 (control) | 3.1 | D |
| Product of Example 4 | 0.4 | A |
| Product of Example 5 | 0.3 | A |
| Product of Example 6 | 1.8 | B |
| Product of Example 7 | 0.3 | A |

As a result, the decomposition products of Examples 4 to 7 had a reduced unpleasant smell compared with the control. Particularly, in the decomposition products obtained in Examples 4, 5, and 7, the unpleasant smell almost completely disappeared, suggesting flavor or taste suitable for drinking.

Example 11

Sensory Evaluation of Bitterness

Bitterness was compared by sensory evaluation among the decomposition products obtained in Examples 4 to 7.

[Method for Sensory Evaluation of Bitterness]

The decomposition products of Examples 4 to 7 and an isohumulone compound (Iso-Extract 30%; Hopsteiner) (control) were evaluated for their bitterness by sensory evaluation using 7 in-house panelists by the following method: aqueous solutions having an approximately neutral pH were prepared such that the amounts of the decomposition products of Examples 4 to 7 each corresponded to the amount of a decomposition product containing 50 ppm isohumulone compounds and the control had 50 ppm isohumulone.

The sensory evaluation was conducted according to evaluation criteria by taking a sip of a few mL of each sample. The results were determined as a mean of evaluation scores of the 7 panelists and indicated in symbols according to the following criteria:

A: very good (the mean was 0 to less than 1)
B: good (the mean was 1 or more to less than 2)
C: slightly poor (the mean was 2 or more to less than 3)
D: very poor (the mean was 3 or more to 4)

[Evaluation Criteria]

TABLE 10

| Evaluation point | Evaluation Criteria | Evaluation score |
|---|---|---|
| Bitterness | No bitterness was felt. | 0 |
| | Bitterness was slightly felt. | 1 |
| | Bitterness was felt. | 2 |
| | Bitterness was strongly felt. | 3 |
| | Undrinkable due to very strongly felt bitterness. | 4 |

[Evaluation Results]

TABLE 11

| | Bitterness score | Evaluation results |
|---|---|---|
| Control | 4 | D |
| Product of Example 4 | 0 | A |
| Product of Example 5 | 0.3 | A |
| Product of Example 6 | 0 | A |
| Product of Example 7 | 0.2 | A |

As a result, bitterness almost completely disappeared in the decomposition products obtained in Examples 4 to 7, suggesting flavor or taste suitable for drinking.

Example 12

Preparation of Samples for Evaluating Physiological Effects

Figure 8:
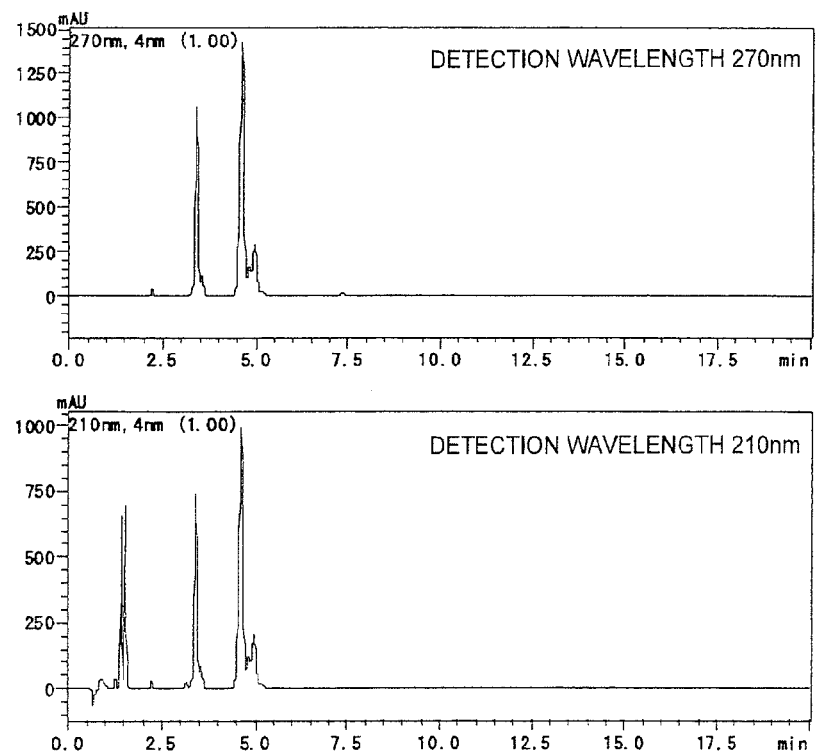
FIG. 8 is a diagram showing HPLC charts of a sample of a decomposition product (Example 12) according to the present invention used in physiological effect evaluation in animals (Example 13).

For evaluating the physiological effects of the strong alkali-thermal decomposition product prepared in Example 1, only the decomposition product was extracted from the decomposition product solution by the following method:

12 N hydrochloric acid was added to 1 L of the decomposition product solution prepared in Example 1, with cooling, to adjust its pH to 2 or lower. Subsequently, a total of 3 extractions were performed with 700 mL, 500 mL, and 500 mL of hexanes. The obtained extracted liquids were combined and washed with saturated saline. Then, residual water was removed with anhydrous sodium sulfate. After hexane removal using a rotary evaporator, the residue was dissolved at a solid content of 50% (w/v) in ethanol. The sample thus prepared was used in evaluation of physiological effects. Moreover, the sample was diluted and subjected to HPLC analysis to confirm that compounds having lower hydrophobicity than that of isohumulone compounds and fatty acids were extracted (FIG. 8).

Example 13

Evaluation of Influence on Fat Accumulation, Etc.
(1)

The decomposition product (strong alkali-thermal decomposition treatment product when the sodium hydroxide concentration was 2 M) obtained in Example 12 was physiologically evaluated using mice. Six C57BL/6J mice (male) (Charles River Laboratories Japan, Inc.) per group were acclimatized to AIN93G feed for 1 week and then set to a total of 2 groups: a high-fat diet group and a group fed with a high-fat diet supplemented with 0.5 w/w % (in terms of solid content) decomposition product obtained in Example 12. Their body weights were measured every week from the start of administration, and the administration was continued for 32 days. During dissection, the weight of visceral fat (indicated in the total weight of peritesticular fat, mesenteric fat, and perirenal fat), the weight of subcutaneous fat, and the weight of the organs, various parameters in blood, etc. were measured.

TABLE 12

Composition of the high fat diet

| | Blend ratio (%) |
|---|---|
| Milk Casein | 29.00 |
| L-cystine | 0.440 |
| Sucrose | 23.28 |
| Safflower oil | 33.50 |
| Cellurose powder | 7.250 |
| AIN93G mineral | 5.080 |
| AIN93G mineral (containing choline) | 1.450 |

Figure 9:
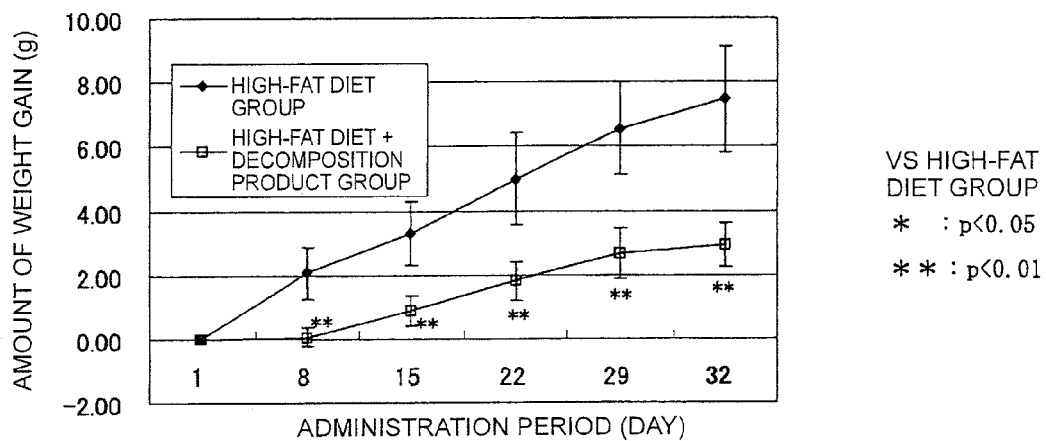
FIG. 9 is a diagram showing the influence of the decomposition product (Example 12) according to the present invention on change in the weights of high-fat diet-fed mice.
Figure 10:
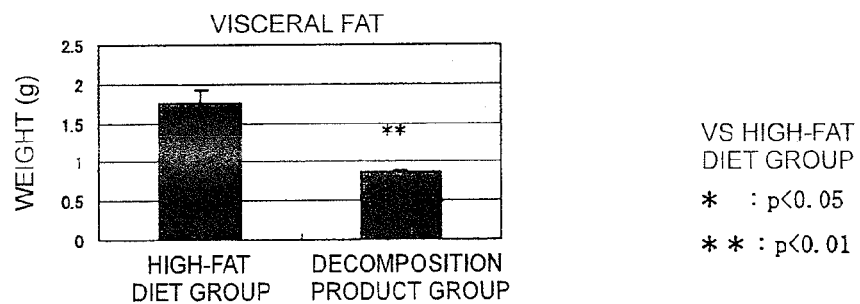
FIG. 10 is a diagram showing the influence of the decomposition product (Example 12) according to the present invention on change in the weight of peritesticular fat in high-fat diet-fed mice.
Figure 11:
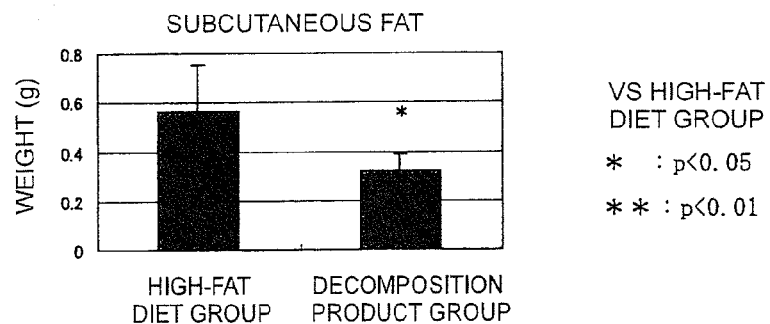
FIG. 11 is a diagram showing the influence of the decomposition product (Example 12) according to the present invention on change in the weight of subcutaneous fat in high-fat diet-fed mice.

As a result, significant suppression effect on weight gain was confirmed for the 0.5% decomposition product addition group compared with the high-fat diet group (FIG. 9). Significant reduction in the weights of visceral fat and subcutaneous fat were also confirmed therefor (FIGS. 10 and 11).

Figure 12:
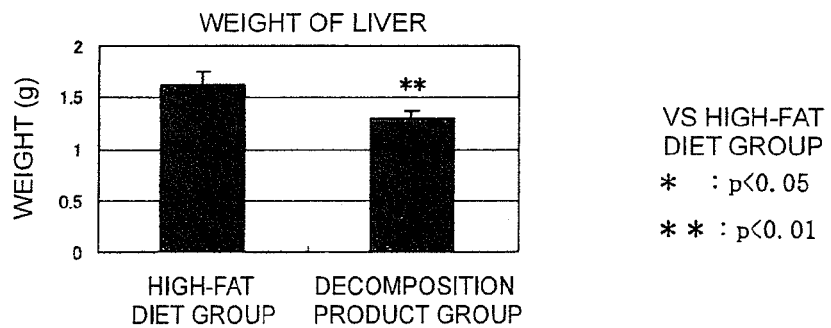
FIG. 12 is a diagram showing the influence of the decomposition product (Example 12) according to the present invention on change in the weight of the liver in high-fat diet-fed mice.
Figure 13:
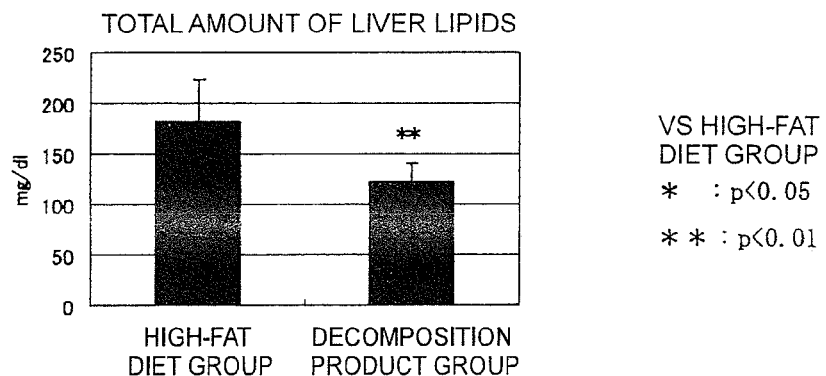
FIG. 13 is a diagram showing the influence of the decomposition product (Example 12) according to the present invention on change in the total amount of liver lipids in high-fat diet-fed mice.
Figure 14:
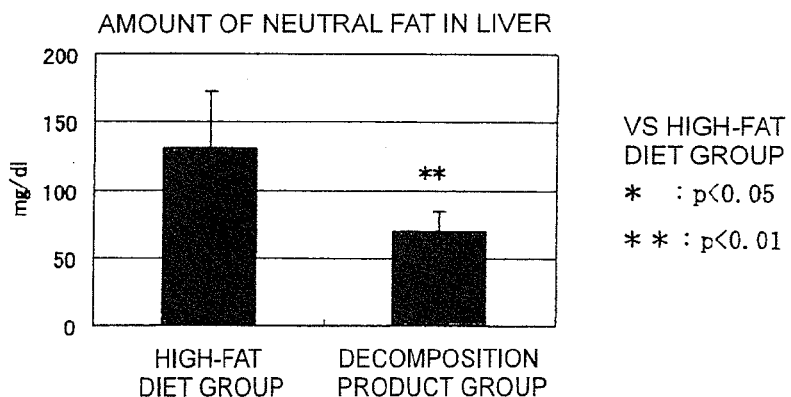
FIG. 14 is a diagram showing the influence of the decomposition product (Example 12) according to the present invention on change in the amount of neutral fat in the liver in high-fat diet-fed mice.
Figure 15:
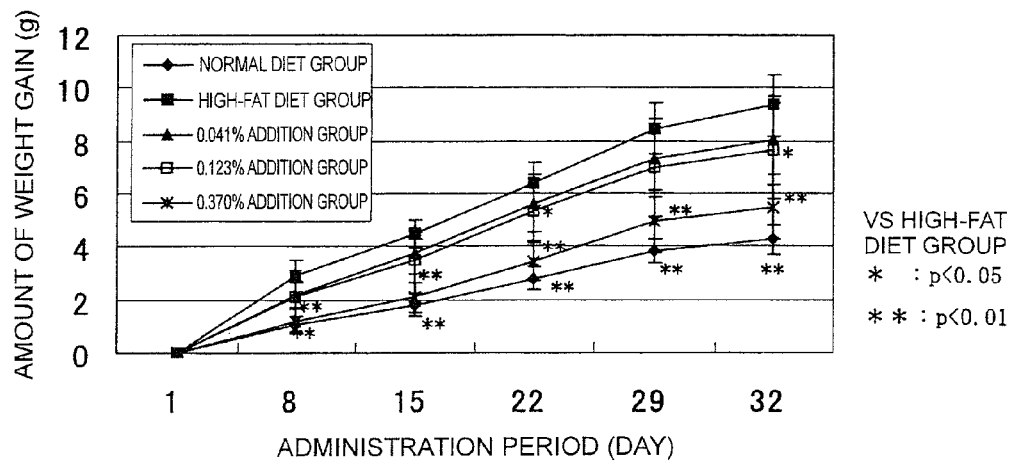
FIG. 15 is a diagram showing the influence of a decomposition product (complex forming component) (Example 4) according to the present invention on change in the weights of high-fat diet-fed mice.
Figure 16:
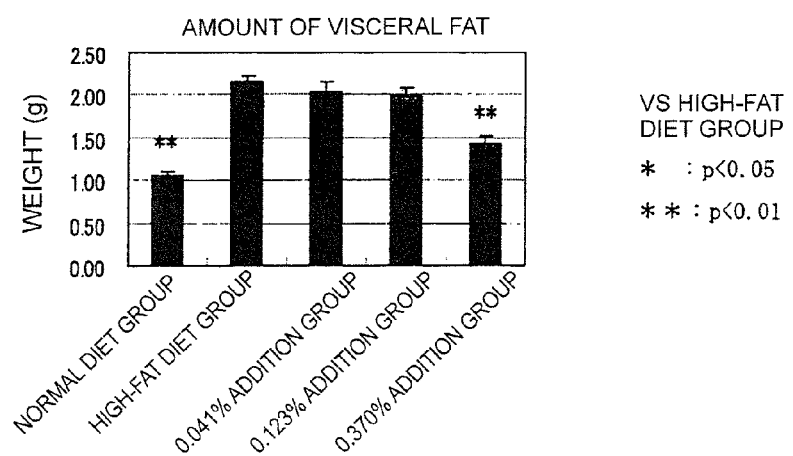
FIG. 16 is a diagram showing the influence of the decomposition product (complex forming component) (Example 4) according to the present invention on change in the weight of visceral fat in high-fat diet-fed mice.
Figure 17:
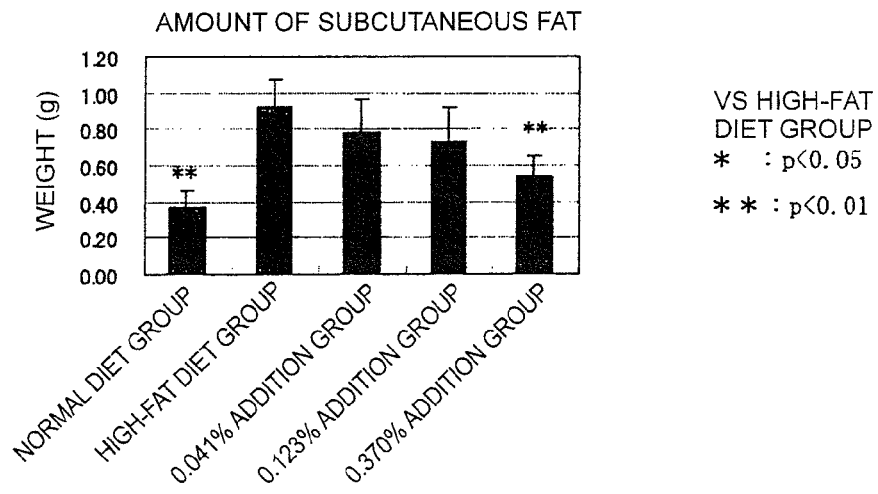
FIG. 17 is a diagram showing the influence of the decomposition product (complex forming component) (Example 4) according to the present invention on change in the weight of subcutaneous fat in high-fat diet-fed mice.
Figure 18:
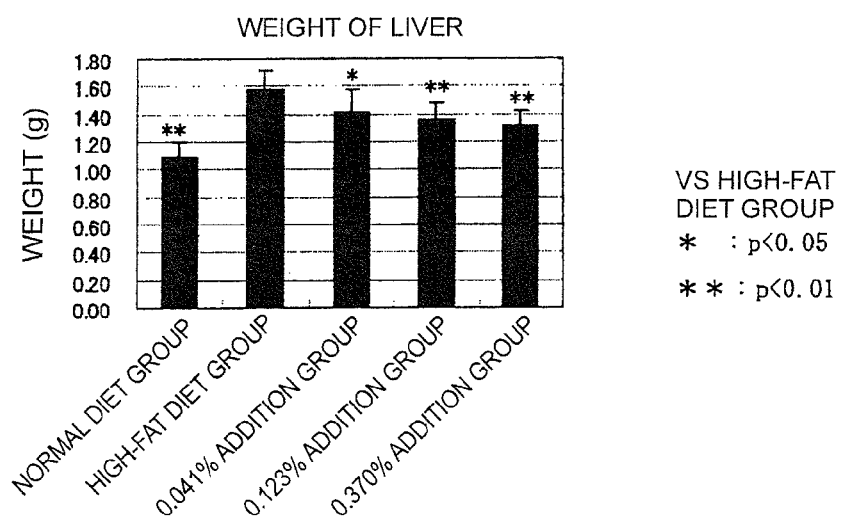
FIG. 18 is a diagram showing the influence of the decomposition product (complex forming component) (Example 4) according to the present invention on change in the weight of the liver in high-fat diet-fed mice.
Figure 19:
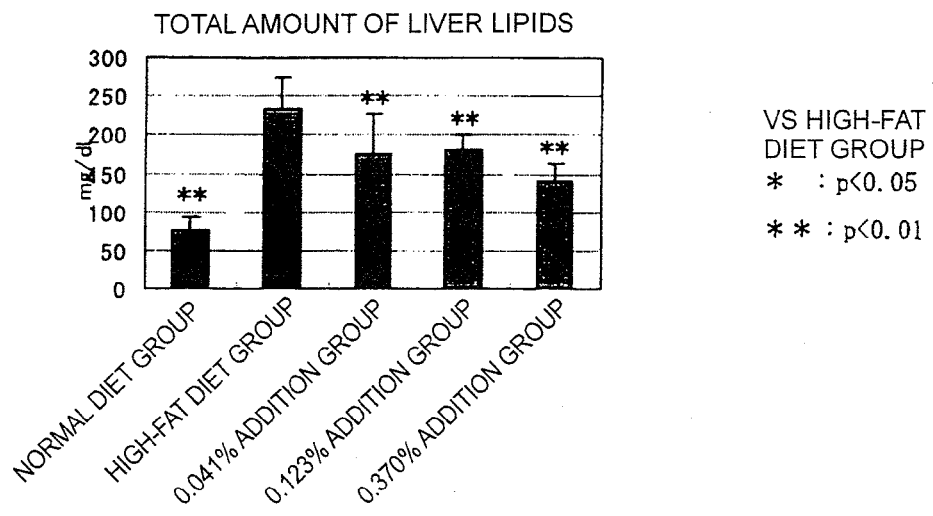
FIG. 19 is a diagram showing the influence of the decomposition product (complex forming component) (Example 4) according to the present invention on change in the total amount of liver lipids in high-fat diet-fed mice.
Figure 20:
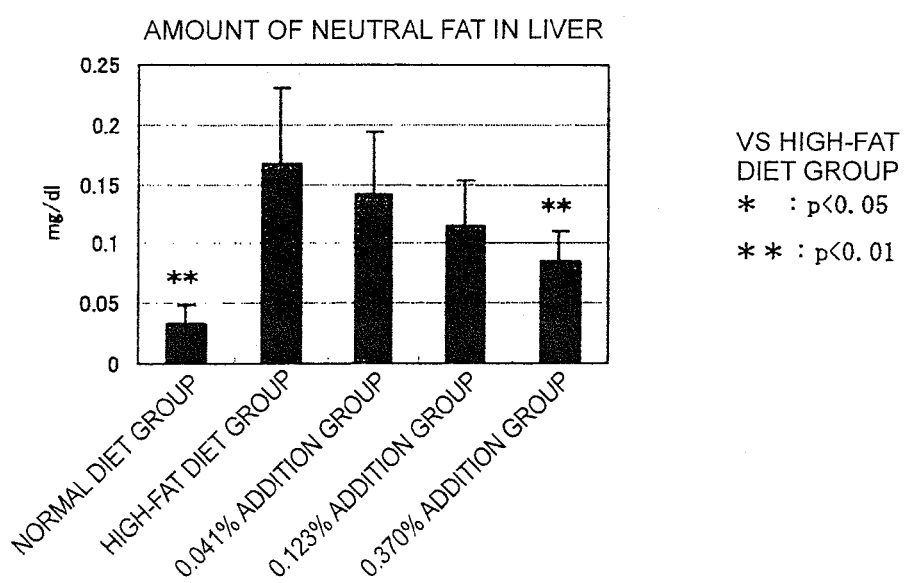
FIG. 20 is a diagram showing the influence of the decomposition product (complex forming component) (Example 4) according to the present invention on change in the amount of neutral fat in the liver in high-fat diet-fed mice.

Moreover, the liver was obtained during dissection, and its weight was measured. As a result, significant decrease compared with the high-fat diet group was confirmed (FIG. 12). Thus, the total cholesterol, neutral fat, and phospholipid content of the liver were measured. Immediately after dissection, the liver was frozen in liquid nitrogen. Then, a portion thereof was obtained after crushing the frozen liver and homogenized under ice cooling using a Teflon (registered trademark) homogenizer in a 9-fold amount (in terms of weight) of saline. Then, lipids were extracted according to the method described in Timothy P. Carr et al., Clinical Biochemistry 26, 39-42, 1993. Specifically, 5 ml of chloroform/methanol (2:1) was added to 1 ml of the liver homogenate, and the mixture was vigorously stirred. Then, 0.5 ml of 0.06 N $H_2SO_4$ was further added thereto, and the mixture was stirred again and then centrifuged to extract a chloroform phase. A portion of the chloroform phase was dried in nitrogen gas, and phospholipids were measured using Phospholipid Test Wako (permanganate ashing method) (manufactured by Wako Pure Chemical Industries, Ltd.). Moreover, another portion of the chloroform phase was mixed with chloroform containing 1% Triton X-100. Then, the mixture was dried in nitrogen gas and suspended in water. Then, its total cholesterol and neutral fat were measured by the method described above. As a result, the total amount of liver lipids and the amount of neutral fat were significantly decreased by the administration of the decomposition product (FIGS. 13 and 14). No significant difference was observed in liver cholesterol and phospholipid.

Example 14

Evaluation of Influence on Fat Accumulation, Etc.
(2)

The physiological effects of the product obtained in Example 4 (sample obtained by removing fatty acids from the decomposition product) were confirmed by the same approach as in Example 13 using mice. In this Example, 5 groups were set: a high-fat diet group, a group fed with a high-fat diet supplemented with 0.370%, 0.123%, or 0.041% (in terms of solid content) product of Example 4, and a normal diet group (AIN93G). The administration period was set to 32 days. As a result, significant weight gain suppression, reduction in the weight of visceral fat, and reduction in the weight of the liver were confirmed (FIGS. 15 to 20).

These results demonstrated that even a product from which a fatty acid has been removed maintains the physiological effects.

Example 15

Evaluation of Influence on Fat Accumulation, Etc.
(3)

The physiological effects of the product obtained in Example 9 (sample obtained by removing fatty acids from the decomposition product and converting the resulting decomposition product to potassium salt) were confirmed by the same approach as in Example 13 using mice. Six C57BL/6J mice (male) (Charles River Laboratories Japan, Inc.) per group were acclimatized to AIN93G feed for 1 week and then set to a total of 2 groups: a high-fat diet group (HFD group) and a group fed with a high-fat diet supplemented with 0.40 w/w % (in terms of solid content) weak alkaline decomposition product (fatty acid-removed decomposition product) obtained in Example 9 (weak alkaline-treated extract group). Their body weights were measured every week from the start of administration, and the administration was continued for 32 days. During dissection, the weight of peritesticular fat and the weight of subcutaneous fat were measured.

Figure 21:
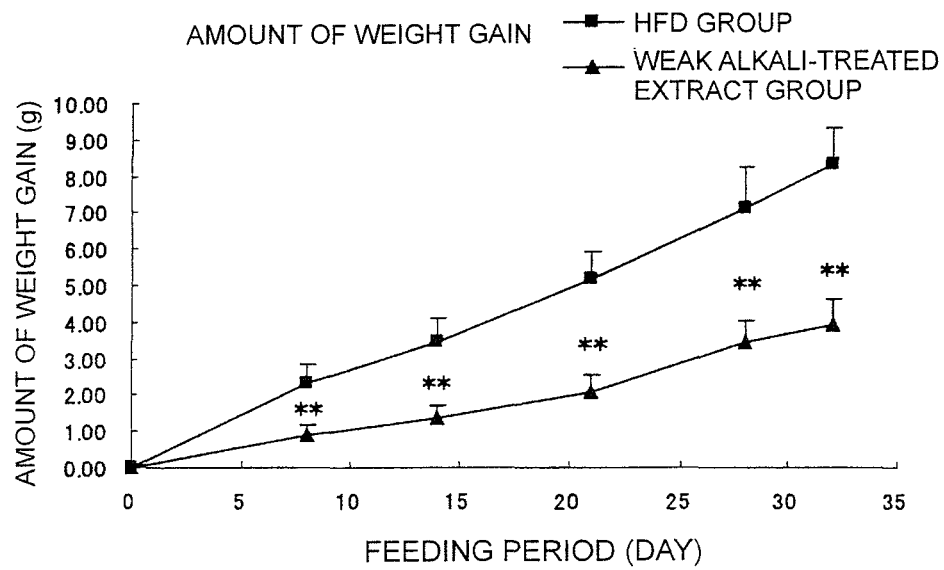
FIG. 21 is a diagram showing the influence of a decomposition product (complex forming component) (Example 9) according to the present invention on change in the weights of high-fat diet-fed mice.
Figure 22:
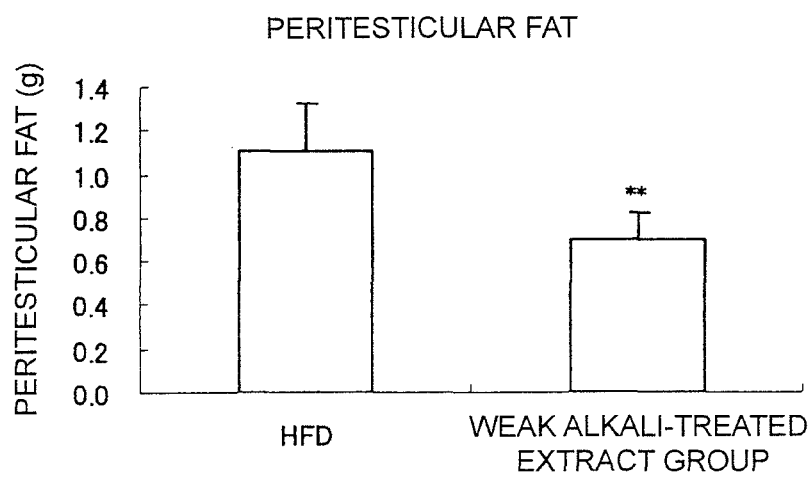
FIG. 22 is a diagram showing the influence of the decomposition product (complex forming component) (Example 9) according to the present invention on change in the weight of peritesticular fat in high-fat diet-fed mice.
Figure 23:
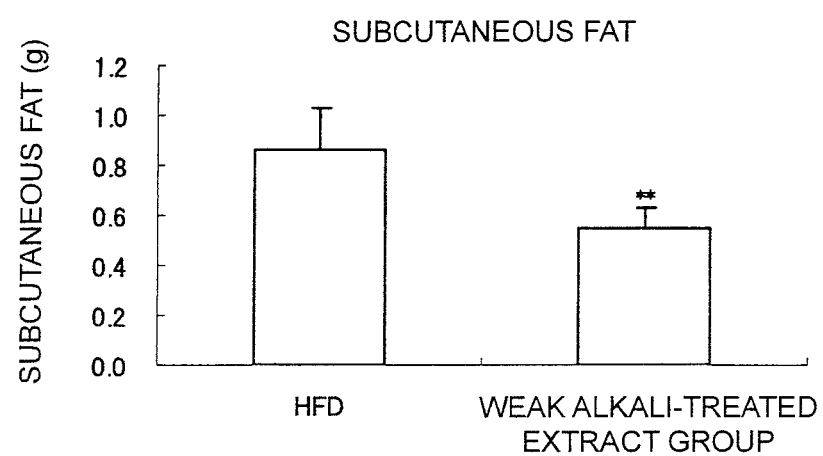
FIG. 23 is a diagram showing the influence of the decomposition product (complex forming component) (Example 9) according to the present invention on change in the weight of subcutaneous fat in high-fat diet-fed mice.

As a result, significant suppression effect on weight gain was confirmed for the 1.25% weak alkaline-treated extract addition group compared with the high-fat diet group (FIG. 21). Significant reduction in the weights of peritesticular fat and subcutaneous fat were also confirmed therein (FIGS. 22 and 23).

Example 16

Investigation on Alkali Concentration

The alkali concentration optimal for the strong alkali-thermal decomposition performed in Example 1 was investigated. An isomerized hop extract (Iso-Extract 30%; Hopsteiner) composed mainly of isohumulone compounds was added at 3 w/v % in terms of the dry weight of the extract to 0 to 2 M sodium hydroxide solutions, and the heating was maintained for 10 minutes. Each sampled solution was assayed by HPLC to calculate the ratio of peak areas of isohumulone compounds to the total peak area. The HPLC analysis was conducted according to the procedures shown in Example 3.

TABLE 13

| Sample No. | Sodium hydroxide concentration (M) | Peak area ratio (peaks of isohumulones/total peaks) |
|---|---|---|
| A1 | 0.5 | 3.4 |
| A2 | 1.0 | 0.9 |
| A3 | 2.0 | 0.3 |
| A4 | 0 | 95.4 |

As a result, the ratio of peak areas of isohumulone compounds to the total peak area was confirmed to be 70% or less when the sodium hydroxide concentration fell within a range of 0.5 to 2.0 M.

Next, each sample (samples "A1" to "A4") obtained by the alkali-heat treatment was subjected to sensory evaluation. The evaluation was conducted according to the procedures described in Example 11.

TABLE 14

| Sample No. | Bitterness score | Evaluation results |
|---|---|---|
| A1 | 0.43 | A |
| A2 | 0.29 | A |
| A3 | 0 | A |
| A4 | 4 | D |

As a result, drastic reduction in bitterness was confirmed when the sodium hydroxide concentration fell within a range of 0.5 to 2.0 M (samples "A1" to "A3").

Example 17

Amount of Extract Added, Heating Temperature, and Heating Time

2 M aqueous sodium hydroxide solutions were separately heated to room temperature to 90° C. An isomerized hop extract (Iso-Extract 30%; Hopsteiner) composed mainly of isohumulone compounds was added thereto at 3 w/v % in terms of the dry weight of the extract. After the addition, the heating time was maintained until several seconds to 24 hours later, and each reaction solution was sampled over time. Their respective supernatants were assayed by HPLC according to the method of Example 3 to calculate the ratio of peak areas of isohumulone compounds to the total peak area. Moreover, sensory evaluation was carried out according to the method described in Example 11. The results were as follows:

TABLE 15

| Sample No. | Heating temperature (° C.) | Heating time (min) | Peak area ratio (isohumulone compound peaks/ total peaks) | Bitterness score | Results of evaluating bitterness |
|---|---|---|---|---|---|
| 1 | 50 | 0 | 79.1 | 3.9 | D |
| 2 | | 5 | 78.2 | 3.9 | D |
| 3 | | 10 | 73.8 | 3.7 | D |
| 4 | | 30 | 55.9 | 2.7 | C |
| 5 | | 60 | 25.8 | 1.6 | B |
| 6 | | 180 | 4.50 | 0.7 | A |
| 7 | | 360 | 1.00 | 0.3 | A |
| 8 | | 1440 | 0.10 | 0.3 | A |
| 9 | 70 | 0 | 90.1 | 4.0 | D |
| 10 | | 5 | 55.0 | 3.1 | C |
| 11 | | 10 | 42.8 | 3.3 | C |
| 12 | | 30 | 8.20 | 1.0 | A |
| 13 | | 60 | 1.90 | 0.1 | A |
| 14 | | 180 | 0.80 | 0.1 | A |
| 15 | | 360 | 0.10 | 0.0 | A |
| 16 | | 1440 | 0.10 | 0.0 | A |
| 17 | 90 | 0 | 81.1 | 4.0 | D |
| 18 | | 5 | 15.6 | 1.4 | B |
| 19 | | 10 | 6.80 | 1.7 | A |
| 20 | | 30 | 1.20 | 0.6 | A |
| 21 | | 60 | 0.50 | 0.3 | A |
| 23 | | 180 | 0.10 | 0.6 | A |
| 24 | | 360 | 0.00 | 0.1 | A |
| 25 | | 1440 | 0.00 | 0.0 | A |
| 26 | Room temperature | 0 | 86.3 | 3.9 | D |
| 27 | | 5 | 31.7 | 2.1 | C |
| 28 | | 10 | 21.3 | 1.9 | B |
| 29 | | 30 | 17.0 | 1.7 | B |
| 30 | | 60 | 13.1 | 1.7 | B |
| 31 | | 180 | 6.30 | 1.3 | A |
| 32 | | 360 | 2.90 | 0.9 | A |
| 33 | | 1440 | 0.40 | 0.4 | A |

As a result, in the sample "27", the peak area ratio reached 70% or less after 5 minutes, and bitterness was reduced. However, the resin was not dissolved in the aqueous layer, and the yield was significantly poor. In the sample "18", the time required for the peak area ratio to reach 70% or less was proportional to the heating temperature and time and shortened with a rise in heating temperature, demonstrating that efficient reduction in bitterness was achieved.

Example 18

Preparation of Strong Alkali-Thermal Decomposition Product from Non-Isomerized Hop Extract A $CO_2$ extract of hops (CO2 Hop Extract; Hopsteiner) composed mainly of humulone, adhumulone, and cohumulone was added at 5 w/v % in terms of the dry weight of the extract into a 2 M aqueous sodium hydroxide solution heated to 80° C. The heating was maintained until 0 to 60 minutes later, and each reaction solution was sampled over time. A pH in the aqueous solution during heating was 13 or higher. The obtained decomposition product solution was pretreated as in Example 3 and then subjected to the HPLC analysis (gradient program (i)) of Example 3 to calculate the ratio of peak areas of humulone compounds and isohumulone compounds to the total peak area. Furthermore, each sample was evaluated for its bitterness by the evaluation method of Example 11. The results were as follows:

TABLE 16

| Heating time (min) | Peak area ratio (Peaks of humulone compounds and isohumulone compound/all peaks) | Results for evaluating bitterness |
|---|---|---|
| 0 | 78.3 | D |
| 5 | 25.8 | C |
| 10 | 8.1 | B |
| 30 | 1.8 | A |
| 60 | 1.9 | A |

Example 19

Preparation of Weak Alkali-Thermal Decomposition Product from Non-Isomerized Hop Extract A $CO_2$ extract of hops (CO2 Hop Extract; Hopsteiner) was added at 5 w/v % in terms of the dry weight of the extract into a 0.5 M aqueous potassium carbonate solution heated to 80° C. The heating was maintained until 0 to 48 minutes later, and each reaction solution was sampled over time. pH in the aqueous solution during heating was 10 to 12. The obtained decomposition product solution was pretreated as in Example 3 and then subjected to the HPLC analysis (gradient program (i)) to calculate the ratio of peak areas of humulone compounds and isohumulone compounds to the total peak area. Furthermore, each sample was evaluated for its bitterness by the evaluation method of Example 11. The results were as follows:

TABLE 17

| Heating time (min) | Peak area ratio (Peaks of humulone compounds and isohumulone compound/all peaks) | Results for evaluating bitterness |
|---|---|---|
| 0 | 83.0 | D |
| 180 | 61.0 | D |
| 1440 | 37.9 | C |
| 2880 | 14.5 | B |

Example 20

Production of Drink Containing Alkaline Decomposition Product

The yellow solid matter (fatty acid-removed) obtained in Example 4 was converted to potassium salt by the method of Example 9. The potassium salt was added at a concentration of 50 mg in terms of solid weight per 350 ml of each drink to commercially available coffee drinks and commercially available black tea drinks (with no sugar or milk) to produce drinks each containing the alkaline decomposition product. Immediately after the addition, the drinks were evaluated and then evaluated again after being left for 1 week at 50° C. The residual rate of the alkaline decomposition product was evaluated by the HPLC analysis of Example 3 to investigate stability.

As a result, the obtained drinks had ignorable bitterness and were stable such that the residual rate of the alkaline decomposition product was 90% or more even after a lapse of 1 week at 50° C.

The invention claimed is:

1. A food additive comprising an alkaline decomposition product of a hop extract,
    wherein said alkaline decomposition product comprises one or more humulinic acids,
    wherein the total mass concentration of iso-alpha- and alpha acids in said alkaline decomposition product is less than or equal to the total mass concentration of humulinic acids in said alkaline decomposition product,
    wherein the iso-alpha- and alpha acids are present in said alkaline decomposition product in an amount such that when said alkaline decomposition product is analyzed by High-Performance Liquid Chromatography (HPLC), the total area of iso-alpha- and alpha acid peaks in said alkaline decomposition product constitutes 30% or less of the total peak area not including beta acids of the alkaline decomposition product, and
    wherein said alkaline decomposition product is in the form of an alkali metal salt.

2. The food additive according to claim 1, wherein one or more fatty acids have been removed from the alkaline decomposition product.

3. The food additive according to claim 1, wherein the alkaline decomposition product comprises a component that forms a complex with a metal ion.

4. The food additive according to claim 2, wherein the total mass concentration of fatty acids in said alkaline decomposition product is 30% or less of the total mass concentration of humulinic acids in said alkaline decomposition product.

5. The food additive according to claim 2, wherein a fatty acid selected from the group consisting of 4-methyl-2-pentenoic acid, 4-methyl-3-pentenoic acid, 4-methylpentanoic acid, and a combination thereof has been removed.

6. A food product comprising the food additive according to claim 1, wherein the food additive is present in said food product in an amount to provide an adult daily dose of between 25 to 780 mg of humulinic acids.

7. A food obtainable by adding an alkaline decomposition product of the hop extract according to claim 1.

8. A method of producing the alkaline decomposition product of the hop extract as defined in claim 1, comprising subjecting a hop extract to an alkaline treatment and subsequently removing a fatty acid formed by the treatment.

9. The production method according to claim 8, comprising adding a metal ion to an alkaline decomposition product of a hop extract and collecting a component that has formed a complex with a metal ion.

10. An agent for suppressing fat accumulation or for suppressing weight gain, comprising the alkaline decomposition product of the hop extract as defined in claim 1 as an active ingredient.

11. The agent for suppressing fat accumulation or for suppressing weight gain according to claim 10, wherein humulinic acids are administered in a range of 25 to 780 mg per day in adult.

12. A method of producing the agent for suppressing fat accumulation or for suppressing weight gain as defined in claim 10, comprising subjecting a hop extract to an alkali-heat treatment and subsequently removing a fatty acid formed by the treatment.

13. The production method according to claim 12, comprising adding a metal ion to an alkaline decomposition product of a hop extract and collecting a component that has formed a complex with the metal ion.

* * * * *